United States Patent
Shelton, IV et al.

(10) Patent No.: US 12,293,432 B2
(45) Date of Patent: May 6, 2025

(54) COOPERATIVE OVERLAYS OF INTERACTING INSTRUMENTS WHICH RESULT IN BOTH OVERLAYS BEING EFFECTED

(71) Applicant: Cilag GmbH International, Zug (CH)

(72) Inventors: Frederick E. Shelton, IV, Hillsboro, OH (US); Shane R. Adams, Lebanon, OH (US); Kevin M. Fiebig, Cincinnati, OH (US); Matthew D. Cowperthwait, Cincinnati, OH (US); Cory G. Kimball, Hamilton, OH (US); Monica L. Z. Rivard, Cincinnati, OH (US); Leonardo N. Rossoni, Rahway, NJ (US); Risto Kojcev, Santa Clara, CA (US); Felix J. Bork, Schnürpflingen (DE)

(73) Assignee: Cilag GmbH International, Zug (CH)

(*) Notice: Subject to any disclaimer, the term of this patent is extended or adjusted under 35 U.S.C. 154(b) by 426 days.

(21) Appl. No.: 17/688,646

(22) Filed: Mar. 7, 2022

(65) Prior Publication Data

US 2022/0331056 A1    Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*G06T 11/00* (2006.01)
*A61B 34/00* (2016.01)
(Continued)

(52) U.S. Cl.
CPC ............. *G06T 11/00* (2013.01); *A61B 34/20* (2016.02); *A61B 34/25* (2016.02); *A61B 34/30* (2016.02);
(Continued)

(58) Field of Classification Search
CPC ......... G06T 11/00; G06T 7/0012; G06T 7/20; G06T 19/006; G06T 2207/10028;
(Continued)

(56) References Cited

U.S. PATENT DOCUMENTS 4,171,700 A    10/1979   Farin
4,849,752 A     7/1989   Bryant
(Continued)

FOREIGN PATENT DOCUMENTS

EP    0408160 A1    1/1991
EP    0473987 A1    3/1992
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Said Broome
*Assistant Examiner* — Andrew Shin
(74) *Attorney, Agent, or Firm* — Condo Roccia Koptiw LLP

(57) ABSTRACT

Apparatuses, systems, and methods for displaying a cooperative overlays based on interacting instruments are disclosed herein. In one aspect, a method for displaying cooperative overlays includes communicatively coupling a first augmented reality display device to a surgical hub; generating, by the first augmented reality display device, a first intraoperative display of a surgical field; displaying, by the
(Continued)

first intraoperative display, a first data overlay based on operation of a first surgical instrument; interacting the first surgical instrument with a second surgical instrument; and displaying, by the first intraoperative display, an indicator of the interaction based on the interaction between the first and second surgical instruments.

18 Claims, 18 Drawing Sheets

(51) Int. Cl.
| | |
|---|---|
| A61B 34/10 | (2016.01) |
| A61B 34/20 | (2016.01) |
| A61B 34/30 | (2016.01) |
| A61B 34/32 | (2016.01) |
| A61B 90/00 | (2016.01) |
| G06F 3/14 | (2006.01) |
| G06F 3/147 | (2006.01) |
| G06T 7/00 | (2017.01) |
| G06T 7/20 | (2017.01) |
| G06T 19/00 | (2011.01) |
| G06V 20/20 | (2022.01) |
| G08B 21/18 | (2006.01) |
| G16H 20/40 | (2018.01) |
| G16H 40/67 | (2018.01) |
| H04L 9/40 | (2022.01) |
| H04L 67/12 | (2022.01) |
| H04W 24/10 | (2009.01) |
| H04W 76/14 | (2018.01) |

(52) U.S. Cl.
CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2090/365* (2016.02); *A61B 2090/371* (2016.02); *A61B 2090/372* (2016.02); *G06T 2210/41* (2013.01)

(58) Field of Classification Search
CPC ....... G06T 2207/30024; G06T 2210/41; G06T 11/60; G06T 7/70; G06T 2200/24; A61B 34/20; A61B 34/25; A61B 34/30; A61B 34/32; A61B 34/76; A61B 90/36; A61B 90/361; A61B 90/37; A61B 90/39; A61B 2034/102; A61B 2034/2055; A61B 2034/2072; A61B 2090/365; A61B 2090/368; A61B 2090/371; A61B 2090/372; A61B 2090/373; A61B 2090/3937; A61B 2090/3975; A61B 17/07292; A61B 90/98; A61B 17/1155; A61B 90/30; A61B 90/94; A61B 2017/00017; A61B 2017/00026; A61B 2017/00084; A61B 2017/00106; A61B 2017/00119; A61B 2017/00128; A61B 2017/00207; A61B 2017/00216; A61B 2017/00809; A61B 2017/00818; A61B 2017/07214; A61B 2017/07271; A61B 2017/1132; A61B 2017/4216; A61B 2018/00898; A61B 2034/2048; A61B 2034/2065; A61B 2034/254; A61B 2034/258; A61B 2090/064; A61B 2090/0807; A61B 2217/005; A61B 2217/007; A61B 17/07207; A61B 34/37; A61B 2017/00115; A61B 2017/00203; A61B 2090/502; G06F 3/14; G06F 3/1454; G06F 3/147; G06F 3/011; G06V 20/20; G06V 10/764; G06V 40/20; G06V 2201/034; G06V 2201/03; G08B 21/182; G16H 20/40; G16H 40/67; G16H 30/40; G16H 40/60; G16H 40/63; G16H 40/20; G16H 50/20; G16H 50/70; G16H 70/20; G16H 30/20; H04L 63/105; H04L 67/12; H04L 67/131; H04L 69/40; H04W 24/10; H04W 76/14; H04W 84/18; H04W 12/06; H04W 12/50; G09G 2380/08

See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,425,375 A | 6/1995 | Chin et al. |
| D379,346 S | 5/1997 | Mieki |
| 5,690,504 A | 11/1997 | Scanlan et al. |
| 5,693,042 A | 12/1997 | Boiarski et al. |
| 5,724,468 A | 3/1998 | Leone et al. |
| 6,049,467 A | 4/2000 | Tamarkin et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,288,606 B1 | 9/2001 | Ekman et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |

(56) References Cited

U.S. PATENT DOCUMENTS

| | | |
|---|---|---|
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| 8,086,008 B2 | 12/2011 | Coste-Maniere et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| 9,017,326 B2 | 4/2015 | Dinardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,935,794 B1 | 4/2018 | Cao et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,019 B2 | 1/2019 | Nawana et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,610,310 B2 | 4/2020 | Todd et al. |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| 11,006,100 B1 | 5/2021 | Douglas |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,114,199 B2 | 9/2021 | Moctezuma De La Barrera |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |

(56) References Cited

U.S. PATENT DOCUMENTS

| | | |
|---|---|---|
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0211930 A1 | 9/2007 | Dolwick et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0192524 A1 | 7/2009 | Itkowitz et al. |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0125149 A1 | 5/2011 | El-Galley et al. |
| 2011/0130689 A1 | 6/2011 | Cohen et al. |
| 2011/0190588 A1 | 8/2011 | Mckay |
| 2011/0245630 A1 | 10/2011 | St. Pierre et al. |
| 2011/0273465 A1 | 11/2011 | Konishi et al. |
| 2011/0298814 A1 | 12/2011 | Mathew et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2013/0031201 A1 | 1/2013 | Kagan et al. |
| 2013/0038707 A1 | 2/2013 | Cunningham et al. |
| 2013/0176220 A1 | 7/2013 | Merschon et al. |
| 2013/0197357 A1* | 8/2013 | Green .................. A61B 90/361 600/424 |
| 2013/0197503 A1 | 8/2013 | Orszulak |
| 2013/0267975 A1 | 10/2013 | Timm et al. |
| 2013/0268283 A1 | 10/2013 | Vann et al. |
| 2013/0303851 A1 | 11/2013 | Griffith et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2015/0019259 A1 | 1/2015 | Qureshi et al. |
| 2015/0070388 A1 | 3/2015 | Sheaffer et al. |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0066184 A1 | 3/2016 | Bhargav-Spantzel et al. |
| 2016/0074096 A1 | 3/2016 | Lieu |
| 2016/0120591 A1 | 5/2016 | Smith et al. |
| 2016/0225192 A1 | 8/2016 | Jones et al. |
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0251305 A1 | 8/2017 | Fathollahi |
| 2017/0252091 A1 | 9/2017 | Honda |
| 2017/0258526 A1 | 9/2017 | Lang |
| 2017/0296213 A1 | 10/2017 | Swensgard et al. |
| 2017/0319259 A1 | 11/2017 | Dunning |
| 2017/0333275 A1 | 11/2017 | Itkowitz et al. |
| 2017/0360466 A1 | 12/2017 | Brown et al. |
| 2018/0014872 A1 | 1/2018 | Dickerson |
| 2018/0032130 A1 | 2/2018 | Meglan |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0173323 A1 | 6/2018 | Harvey et al. |
| 2018/0221005 A1 | 8/2018 | Hamel et al. |
| 2018/0228528 A1 | 8/2018 | Fraasch et al. |
| 2018/0243573 A1 | 8/2018 | Yoder et al. |
| 2018/0262916 A1 | 9/2018 | Polley et al. |
| 2018/0263557 A1 | 9/2018 | Kahlman |
| 2018/0289338 A1 | 10/2018 | Meador et al. |
| 2018/0317826 A1 | 11/2018 | Muhsin et al. |
| 2018/0333207 A1 | 11/2018 | Moctezuma De la Barrera |
| 2018/0368930 A1 | 12/2018 | Esterberg et al. |
| 2019/0035153 A1 | 1/2019 | Dange |
| 2019/0038362 A1 | 2/2019 | Nash et al. |
| 2019/0069957 A1 | 3/2019 | Barral et al. |
| 2019/0104919 A1 | 4/2019 | Shelton, IV et al. |
| 2019/0125361 A1 | 5/2019 | Shelton, IV et al. |
| 2019/0125451 A1 | 5/2019 | Srimohanarajah et al. |
| 2019/0125454 A1 | 5/2019 | Stokes et al. |
| 2019/0125455 A1 | 5/2019 | Shelton, IV et al. |
| 2019/0125459 A1 | 5/2019 | Shelton et al. |
| 2019/0183576 A1 | 6/2019 | Fahim et al. |
| 2019/0183591 A1 | 6/2019 | Johnson et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201046 A1 | 7/2019 | Shelton, IV et al. |
| 2019/0201102 A1 | 7/2019 | Shelton, IV et al. |
| 2019/0201116 A1 | 7/2019 | Shelton, IV et al. |
| 2019/0201127 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0205001 A1 | 7/2019 | Messerly et al. |
| 2019/0206004 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206565 A1 | 7/2019 | Shelton, IV |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015895 A1 | 1/2020 | Frielinghaus et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015902 A1 | 1/2020 | Scheib et al. |
| 2020/0015906 A1 | 1/2020 | Scheib et al. |
| 2020/0015907 A1 | 1/2020 | Scheib |

(56) References Cited

U.S. PATENT DOCUMENTS

| | | |
|---|---|---|
| 2020/0015914 A1 | 1/2020 | Scheib et al. |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0093357 A1 | 3/2020 | Scott et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237031 A1 | 7/2020 | Daniels et al. |
| 2020/0237452 A1 | 7/2020 | Wolf et al. |
| 2020/0268469 A1 | 8/2020 | Wolf et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0322516 A1 | 10/2020 | Doser et al. |
| 2020/0342228 A1 | 10/2020 | Prevrhal et al. |
| 2020/0359892 A1 | 11/2020 | Rollins et al. |
| 2020/0384287 A1 | 12/2020 | Hetz |
| 2020/0405529 A1 | 12/2020 | Taylor et al. |
| 2021/0121246 A1 | 4/2021 | Gudalo |
| 2021/0128254 A1 | 5/2021 | Geric et al. |
| 2021/0169578 A1 | 6/2021 | Calloway et al. |
| 2021/0169581 A1 | 6/2021 | Calloway et al. |
| 2021/0174956 A1 | 6/2021 | Mcginley et al. |
| 2021/0192759 A1* | 6/2021 | Lang ..................... A61B 34/20 |
| 2021/0193681 A1 | 6/2021 | Baek |
| 2021/0196381 A1 | 7/2021 | Eckert et al. |
| 2021/0196383 A1 | 7/2021 | Shelton, IV et al. |
| 2021/0203889 A1 | 7/2021 | Fung et al. |
| 2021/0205020 A1 | 7/2021 | Shelton, IV et al. |
| 2021/0212717 A1 | 7/2021 | Yates et al. |
| 2021/0236755 A1 | 8/2021 | King et al. |
| 2021/0259789 A1 | 8/2021 | Wright et al. |
| 2021/0264680 A1 | 8/2021 | Cvetko et al. |
| 2021/0267664 A1 | 9/2021 | Lennartz et al. |
| 2021/0306691 A1 | 9/2021 | Thomas et al. |
| 2021/0307861 A1* | 10/2021 | Hufford ............. H04N 21/8352 |
| 2021/0313052 A1 | 10/2021 | Makrinich et al. |
| 2021/0333864 A1 | 10/2021 | Harvey et al. |
| 2021/0346092 A1 | 11/2021 | Redmond et al. |
| 2021/0369394 A1 | 12/2021 | Braido et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0151704 A1 | 5/2022 | Nikou |
| 2022/0155910 A1 | 5/2022 | Jeong |
| 2022/0160428 A1 | 5/2022 | Murray et al. |
| 2022/0188545 A1 | 6/2022 | Nagar et al. |
| 2022/0237878 A1 | 7/2022 | Tartz et al. |
| 2022/0257333 A1 | 8/2022 | Haider |
| 2022/0261056 A1 | 8/2022 | Motoi et al. |
| 2022/0283631 A1 | 9/2022 | Peng |
| 2022/0287676 A1 | 9/2022 | Steines et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0387128 A1 | 12/2022 | Bail et al. |
| 2023/0038130 A1 | 2/2023 | Cvetko et al. |
| 2023/0072423 A1 | 3/2023 | Osborn et al. |
| 2023/0121709 A1 | 4/2023 | Xu et al. |
| 2023/0157757 A1 | 5/2023 | Braido et al. |
| 2023/0157762 A1 | 5/2023 | Braido et al. |
| 2024/0130795 A1 | 4/2024 | Clayton et al. |
| 2024/0138931 A1 | 5/2024 | Lefauconnier |
| 2024/0176441 A1 | 5/2024 | Yang et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| EP | 3053279 A1 | 8/2016 |
| EP | 3387982 A1 | 10/2018 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | 2016154557 A1 | 9/2016 |
| WO | WO-2017058617 A2 | 4/2017 |
| WO | WO-2018116247 A1 | 6/2018 |
| WO | WO-2019215354 A1 | 11/2019 |
| WO | 2020112217 A1 | 6/2020 |
| WO | 2020180917 A1 | 9/2020 |
| WO | WO-2021044136 A1 | 3/2021 |
| WO | 2021/146313 A1 | 7/2021 |

OTHER PUBLICATIONS

IEEE Std 802.Mar. 2012 (Revision of IEEE Std 802.Mar. 2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

(56) References Cited

OTHER PUBLICATIONS

Zhu et al. "Haptic-feedback smart glove as a creative human-machine interface (HMI) for virtual/augmented reality applications," Sci. Adv, vol. 6, No. 19, May 8, 2020.
Qian, et al., "A Review of Augmented Reality in Robotic-Assisted Surgery", IEEE Transactions on Medical Robotics and Bionics, IEEE, vol. 2, No. 1, pp. 1-16, Feb. 2020.
Yu et al., "Skin-Integrated Wireless Haptic Interfaces for Virtual and Augmented Reality," Nature, vol. 575, pp. 473-479, Nov. 21, 2019.
Li et al., "Wearable Energy Harvesters Generating Electricity From Low-Frequency Human Limb Movement," Microsystems & Nanoengineering (2018), vol. 4(24), 13 pages.
Vávra et al., "Recent Development of Augmented Reality in Surgery: A Review", Journal of Healthcare Engineering, vol. 2017, Article ID 4574172, Aug. 21, 2017, pp. 1-9.

\* cited by examiner

COOPERATIVE OVERLAYS OF INTERACTING INSTRUMENTS WHICH RESULT IN BOTH OVERLAYS BEING EFFECTED

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices including energy, staplers, or combined energy and staplers. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various aspects, the present disclosure provides a method for displaying a cooperative overlay of interacting instruments. In some aspects, the method includes communicatively coupling a first augmented reality display device to a surgical hub; generating, by the first augmented reality display device, a first intraoperative display of a surgical field; displaying, by the first intraoperative display, a first data overlay based on operation of a first surgical instrument; interacting the first surgical instrument with a second surgical instrument; and displaying, by the first intraoperative display, an indicator of the interaction based on the interaction between the first and second surgical instruments.

In various aspects, the present disclosure provides a system for displaying a cooperative overlay of interacting instruments. In some aspects, the system includes a first augmented reality display device configured to generate a first intraoperative display of a surgical field; a first surgical instrument; a second surgical instrument; and a surgical hub communicatively coupled to the first display device. In one aspect, the first intraoperative display displays a first data overlay based on operation of the first surgical instrument. In another aspect, an interaction of the first surgical instrument and the second surgical instrument causes the first intraoperative display to display an indicator of the interaction.

FIGURES

The various aspects described herein, both as to organization and methods of operation, together with further objects and advantages thereof, may best be understood by reference to the following description, taken in conjunction with the accompanying drawings as follows.

FIGS. 16A, 16B, 16C, and 16D illustrate an exemplary intraoperative display displaying the performance of an anastomosis procedure using an anvil and a device deck, according to one aspect of this disclosure.

Figure 17:
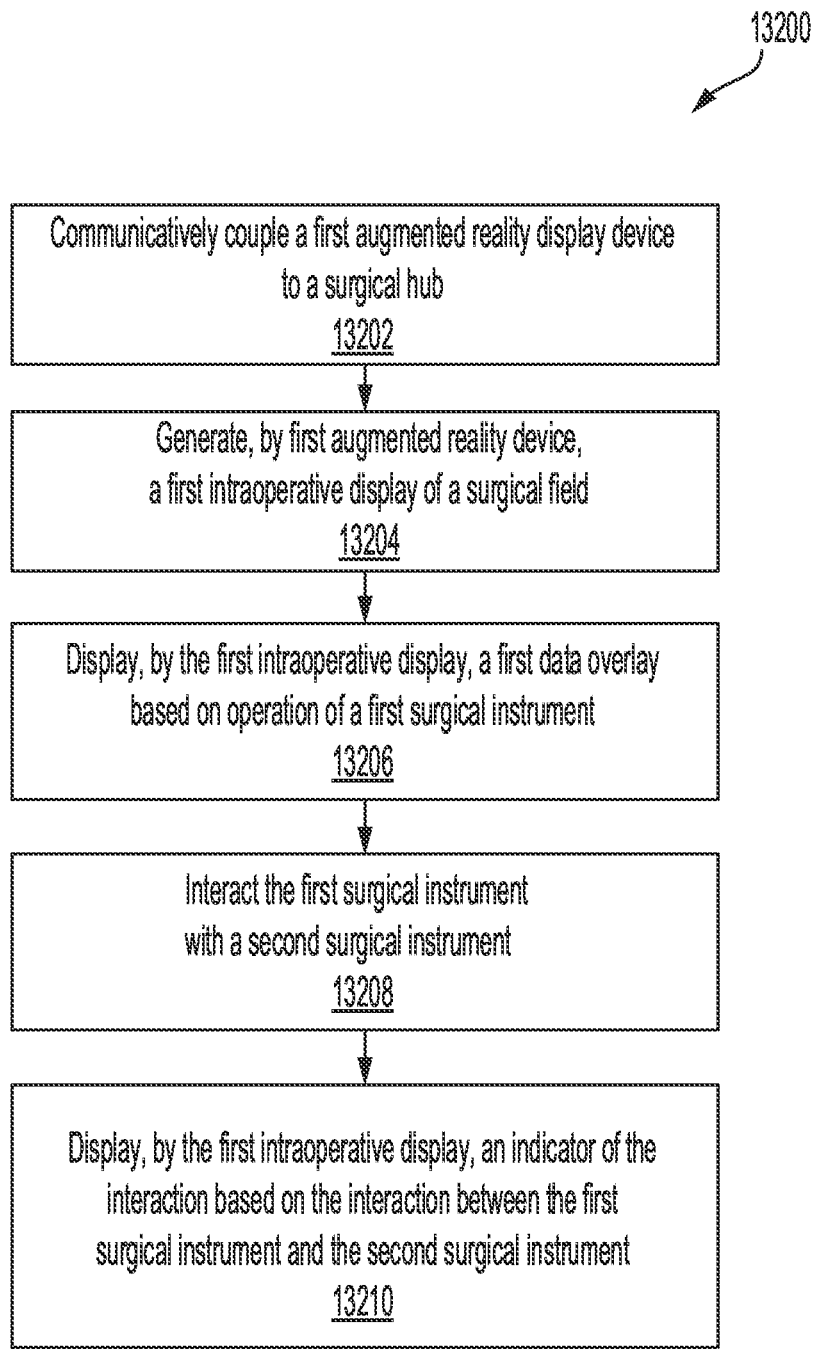

FIG. 17, illustrates a flowchart of method for displaying a cooperative overlay of interacting instruments, according to one aspect of this disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Applicant of the present application owns the following U.S. patent applications filed concurrently herewith, the disclosures of each of which is herein incorporated by reference in its entirety:

U.S. patent application Ser. No. 17/688,589, titled METHOD FOR INTRAOPERATIVE DISPLAY FOR SURGICAL SYSTEMS;

U.S. patent application Ser. No. 17/688,597, titled UTILIZATION OF SURGICAL DATA VALUES AND SITUATIONAL AWARENESS TO CONTROL THE OVERLAY IN SURGICAL FIELD VIEW;

U.S. patent application Ser. No. 17/688,605, titled SELECTIVE AND ADJUSTABLE MIXED REALITY OVERLAY IN SURGICAL FIELD VIEW;

U.S. patent application Ser. No. 17/688,615, titled RISK BASED PRIORITIZATION OF DISPLAY ASPECTS IN SURGICAL FIELD VIEW;

U.S. patent application Ser. No. 17/688,626, titled SYSTEMS AND METHODS FOR CONTROLLING SURGICAL DATA OVERLAY;

U.S. patent application Ser. No. 17/688,633, titled SYSTEMS AND METHODS FOR CHANGING DISPLAY OVERLAY OF SURGICAL FIELD VIEW BASED ON TRIGGERING EVENTS;

U.S. patent application Ser. No. 17/688,638, titled CUSTOMIZATION OF OVERLAID DATA AND CONFIGURATION;

U.S. patent application Ser. No. 17/688,641, titled INDICATION OF THE COUPLE PAIR OF REMOTE CONTROLS WITH REMOTE DEVICES FUNCTIONS;

U.S. patent application Ser. No. 17/688,651, titled ANTICIPATION OF INTERACTIVE UTILIZATION OF COMMON DATA OVERLAYS BY DIFFERENT USERS;

U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN;

U.S. patent application Ser. No. 17/688,655, titled SYSTEM AND METHOD FOR TRACKING A PORTION OF THE USER AS A PROXY FOR NON-MONITORED INSTRUMENT;

U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;

U.S. patent application Ser. No. 17/688,660, titled COOPERATION AMONG MULTIPLE DISPLAY SYSTEMS TO PROVIDE A HEALTHCARE USER CUSTOMIZED INFORMATION;

U.S. patent application Ser. No. 17/688,663, titled INTRAOPERATIVE DISPLAY FOR SURGICAL SYSTEMS;

U.S. patent application Ser. No. 17/688,667, titled ADAPTATION AND ADJUSTABILITY OR OVERLAID INSTRUMENT INFORMATION FOR SURGICAL SYSTEMS;

U.S. patent application Ser. No. 17/688,671, titled MIXED REALITY FEEDBACK SYSTEMS THAT COOPERATE TO INCREASE EFFICIENT PERCEPTION OF COMPLEX DATA FEEDS.

Applicant of this application owns the following U.S. patent applications, the disclosure of each of which is herein incorporated by reference in its entirety:

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;

U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

Figure 1:
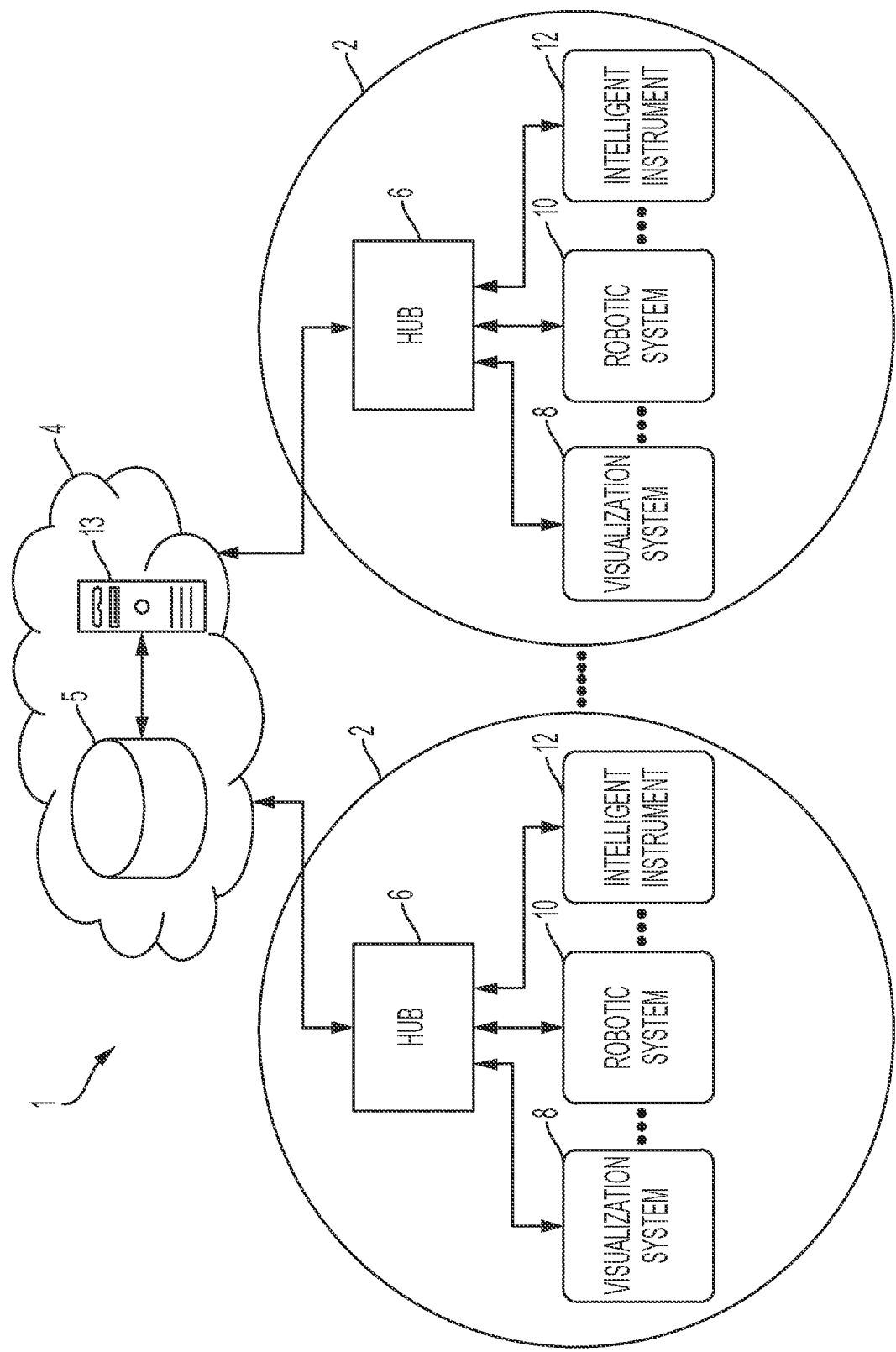
FIG. 1 is a block diagram of a computer-implemented interactive surgical system, according to one aspect of this disclosure.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
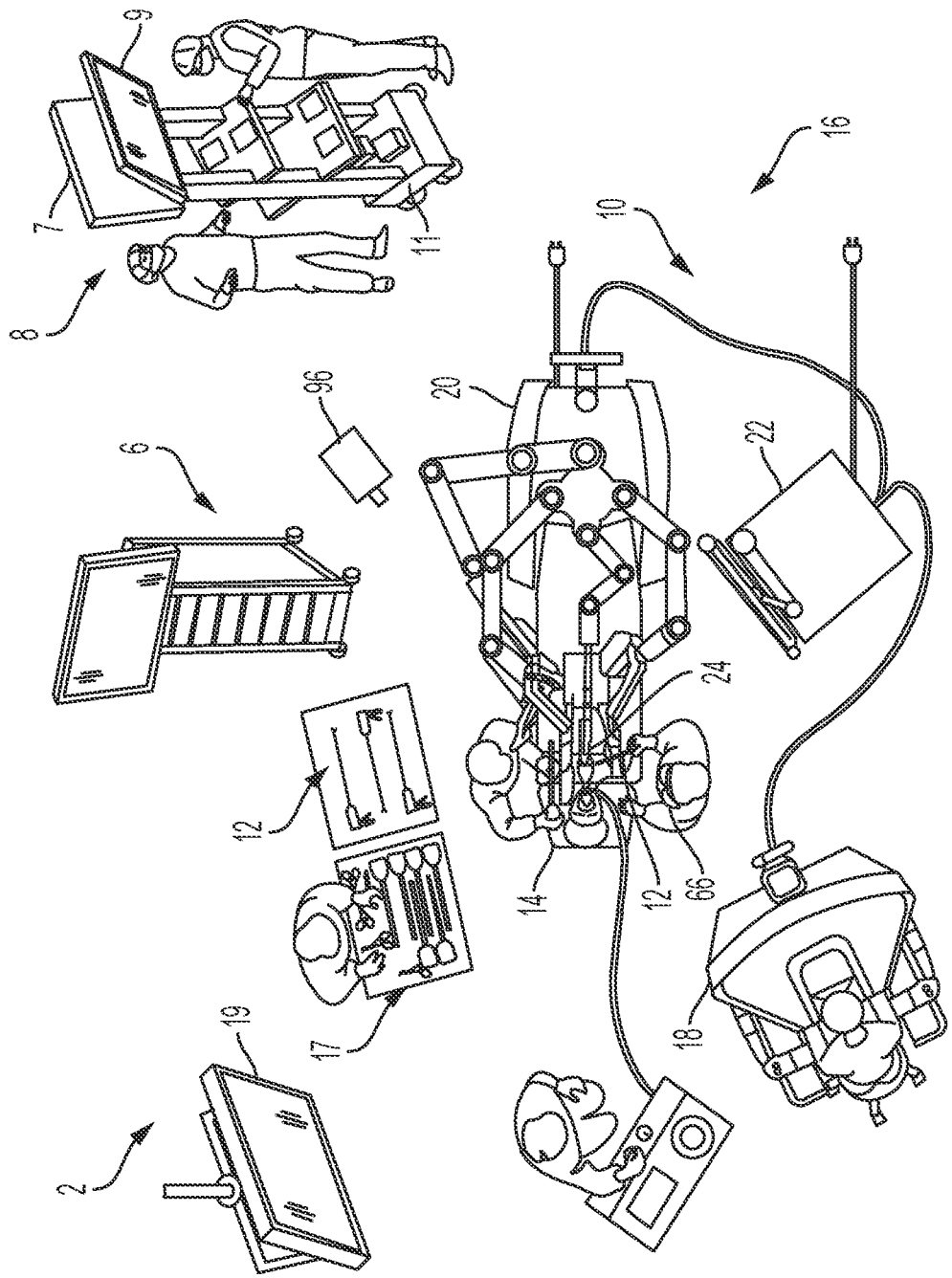
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
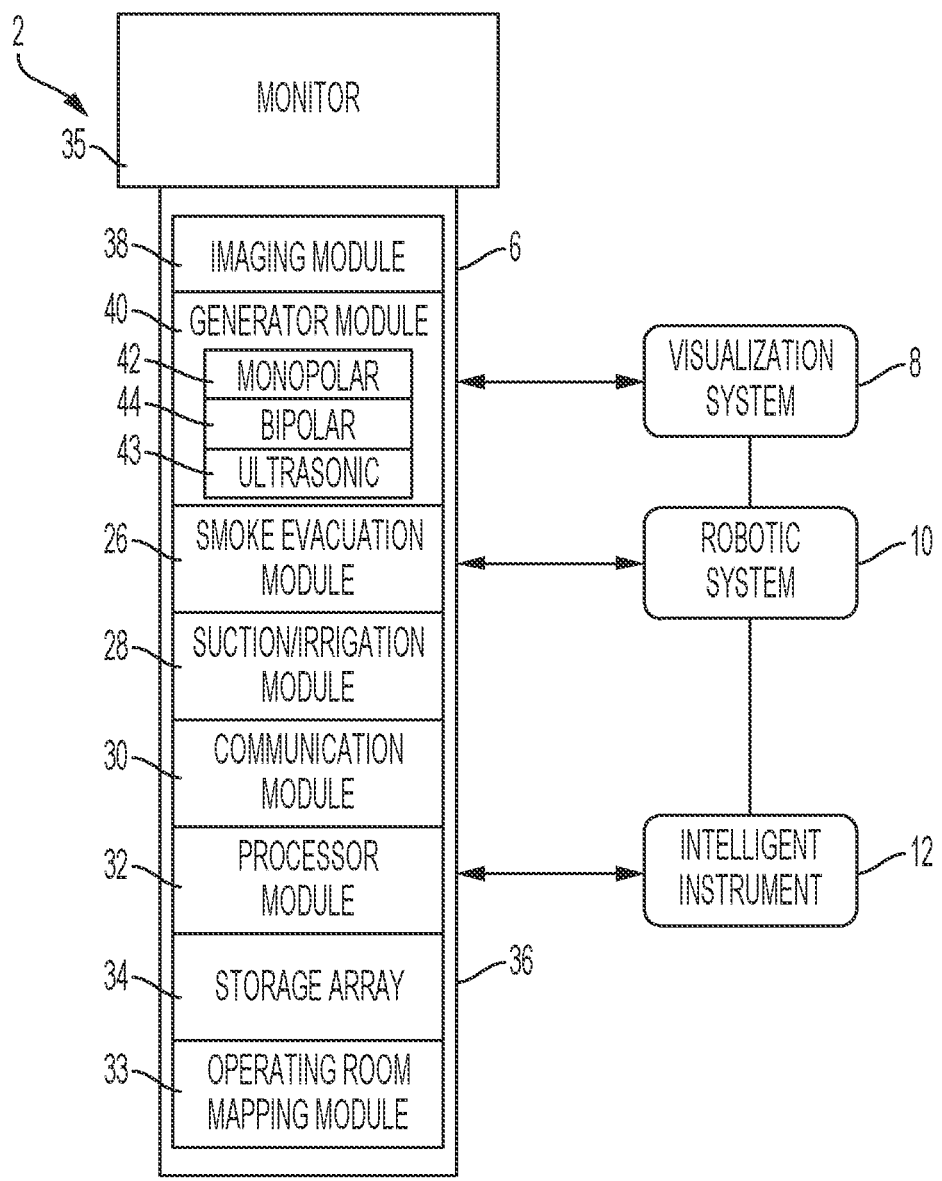
FIG. 3 is a surgical hub paired with a visualization system, a robotic system, and an intelligent instrument, according to one aspect of this disclosure.
Figure 10:
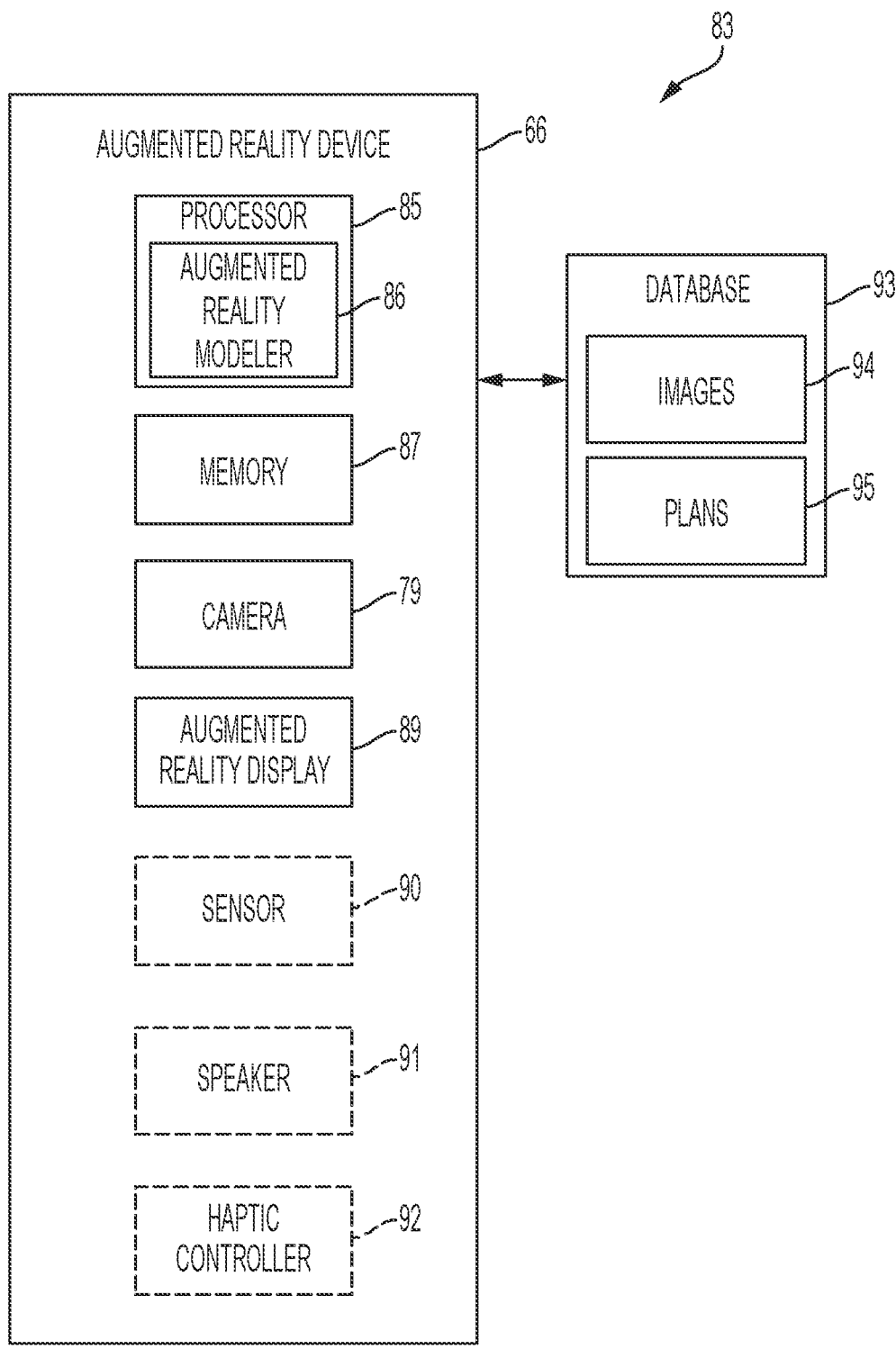
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
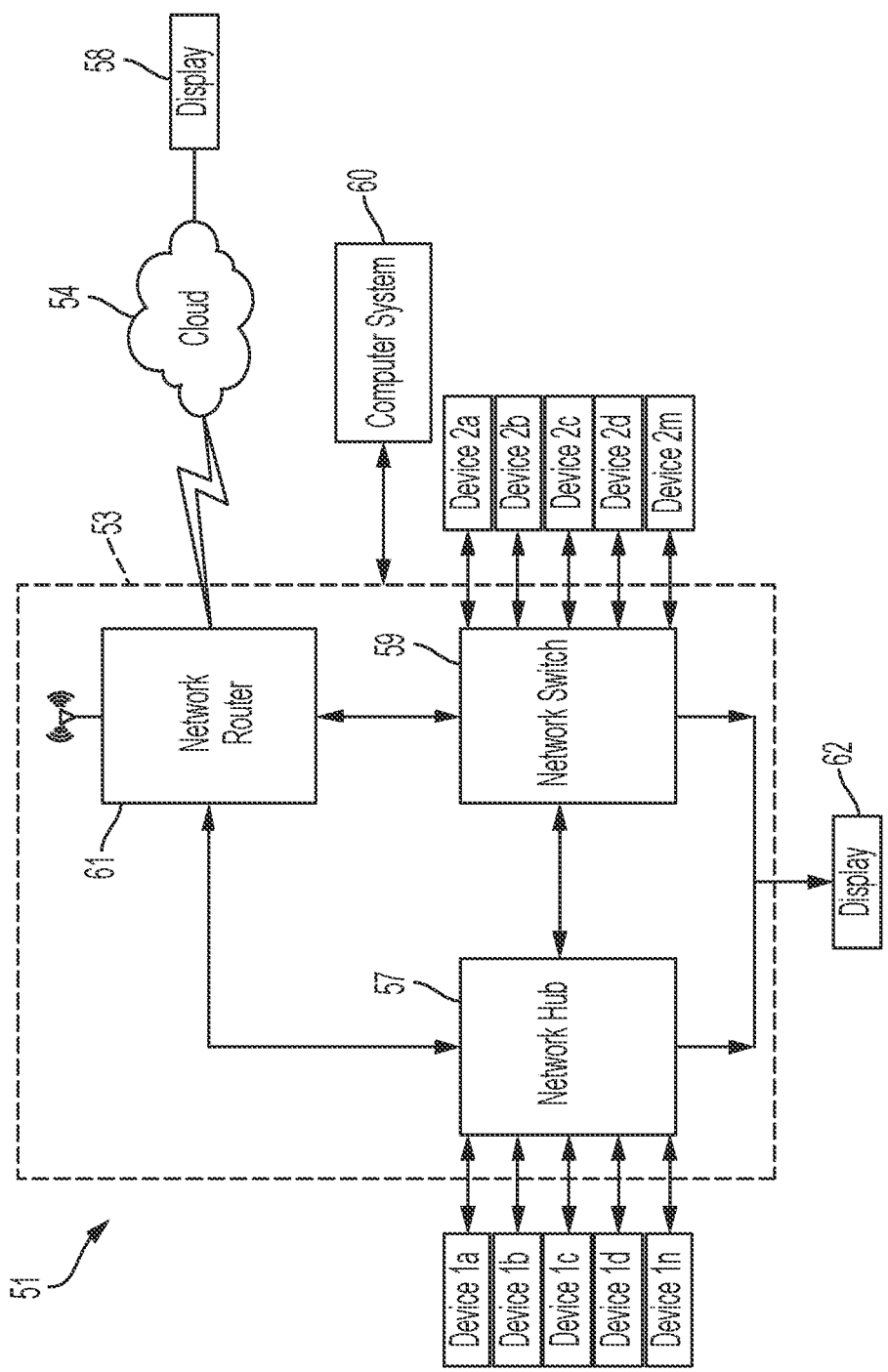
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1a-1n in the operating theater may be coupled to the modular communication hub 53. The network hub 57 and/or the network switch 59 may be coupled to a network router 61 to connect the devices 1a-1n to the cloud 54 or the local computer system 60. Data associated with the devices 1a-1n may be transferred to cloud-based computers via the router for remote data processing and manipulation. The operating theater devices 1a-1n may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
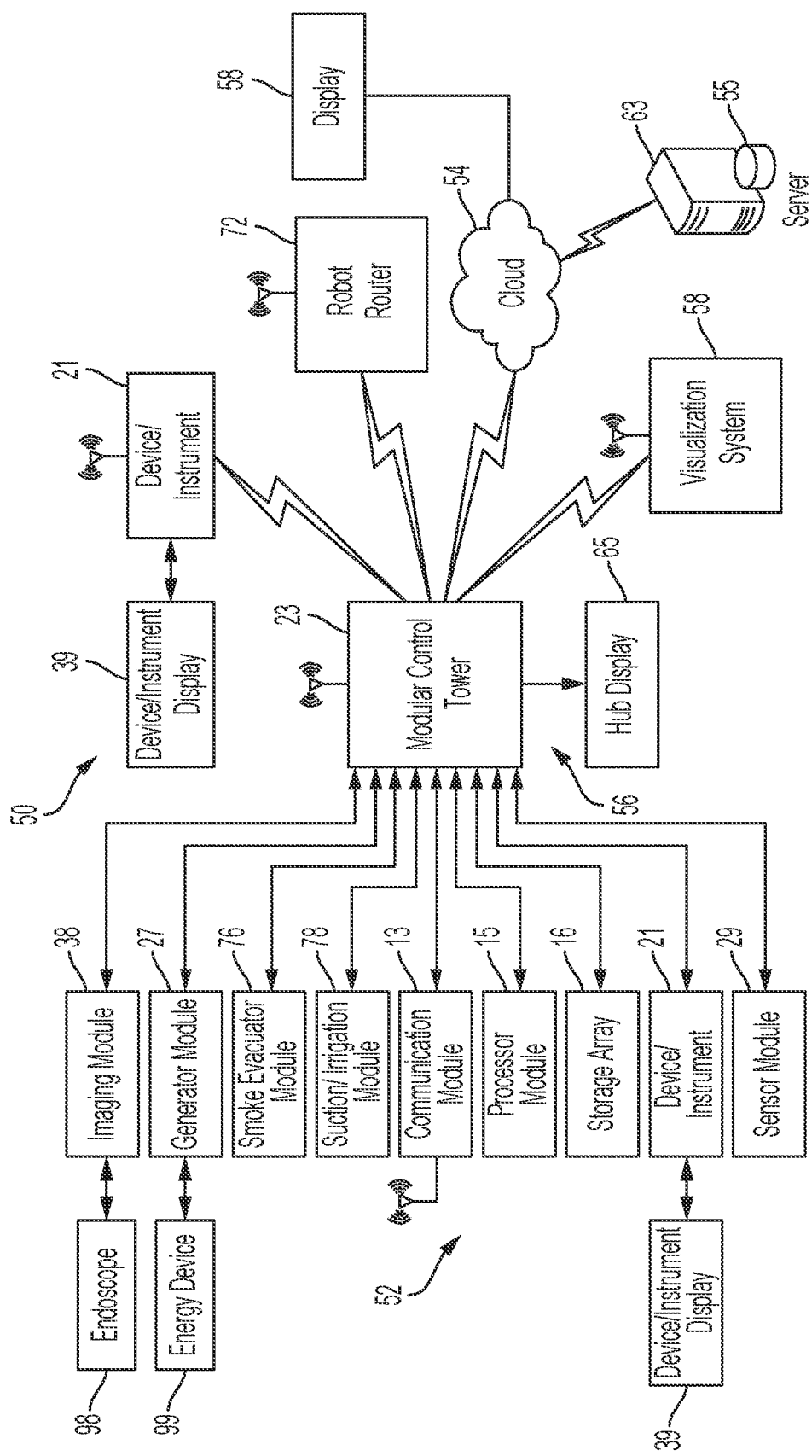
FIG. 5 illustrates a computer-implemented interactive surgical system, according to one aspect of this disclosure.
Figure 6:
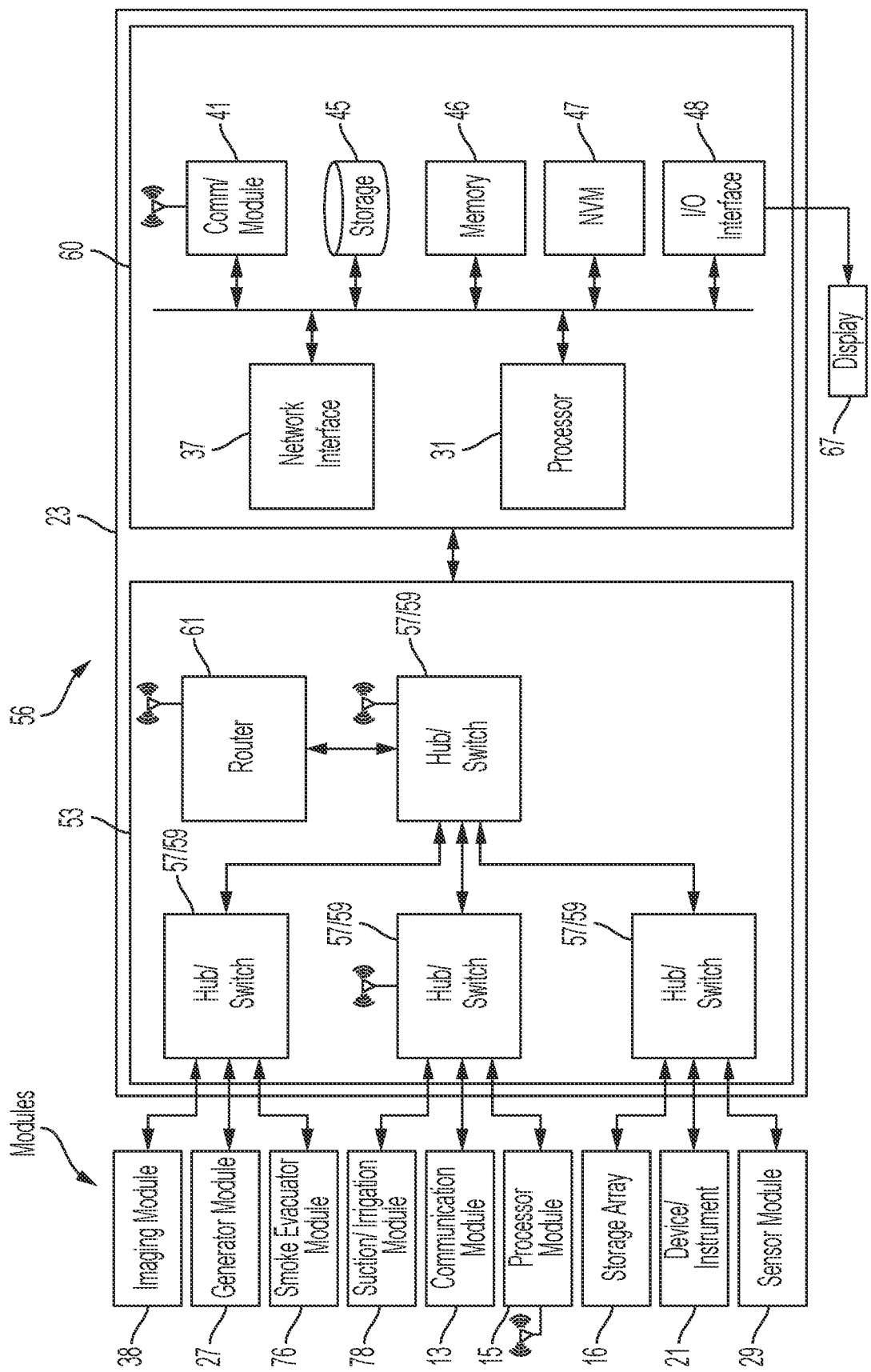
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
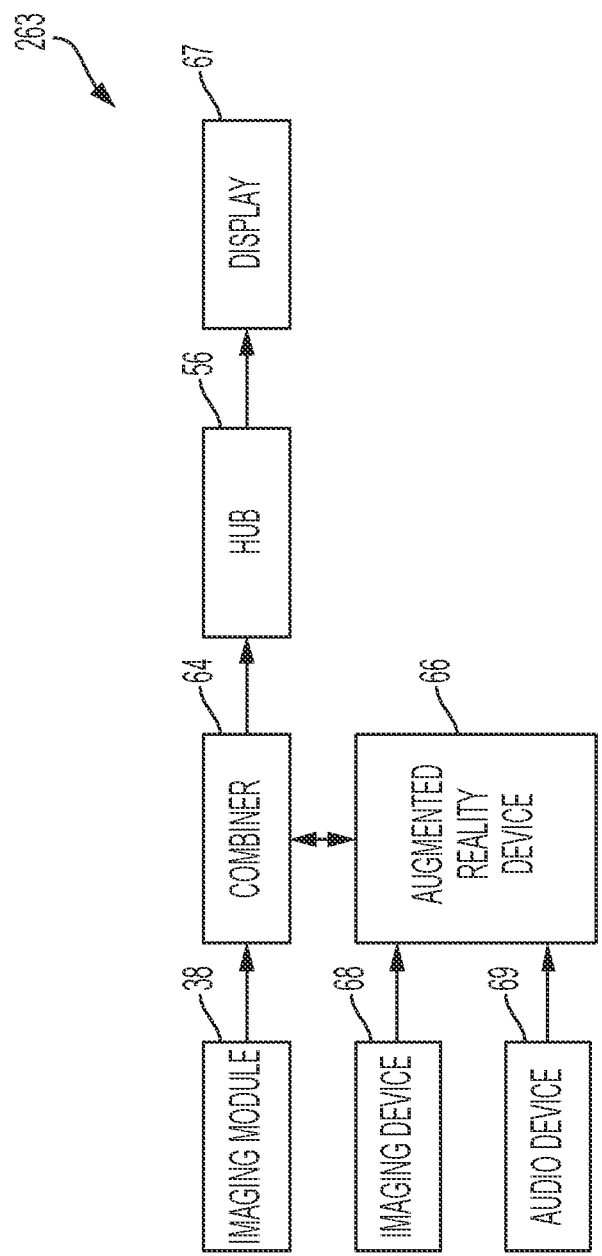
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
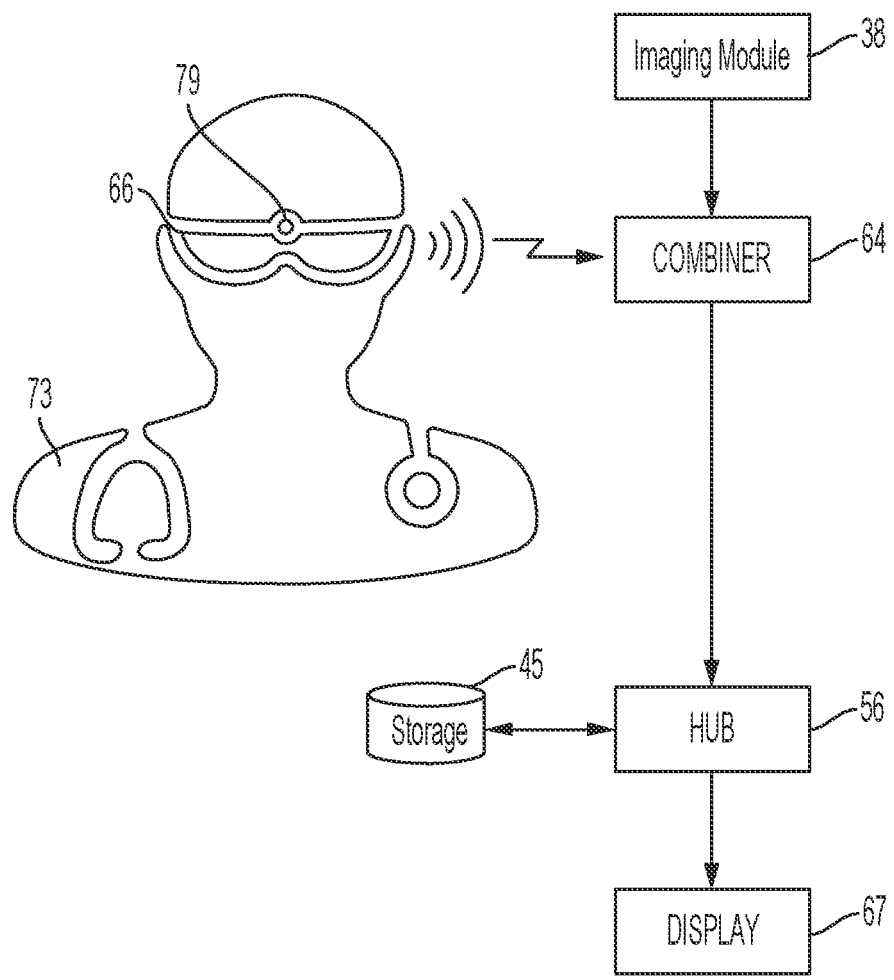
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure—ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
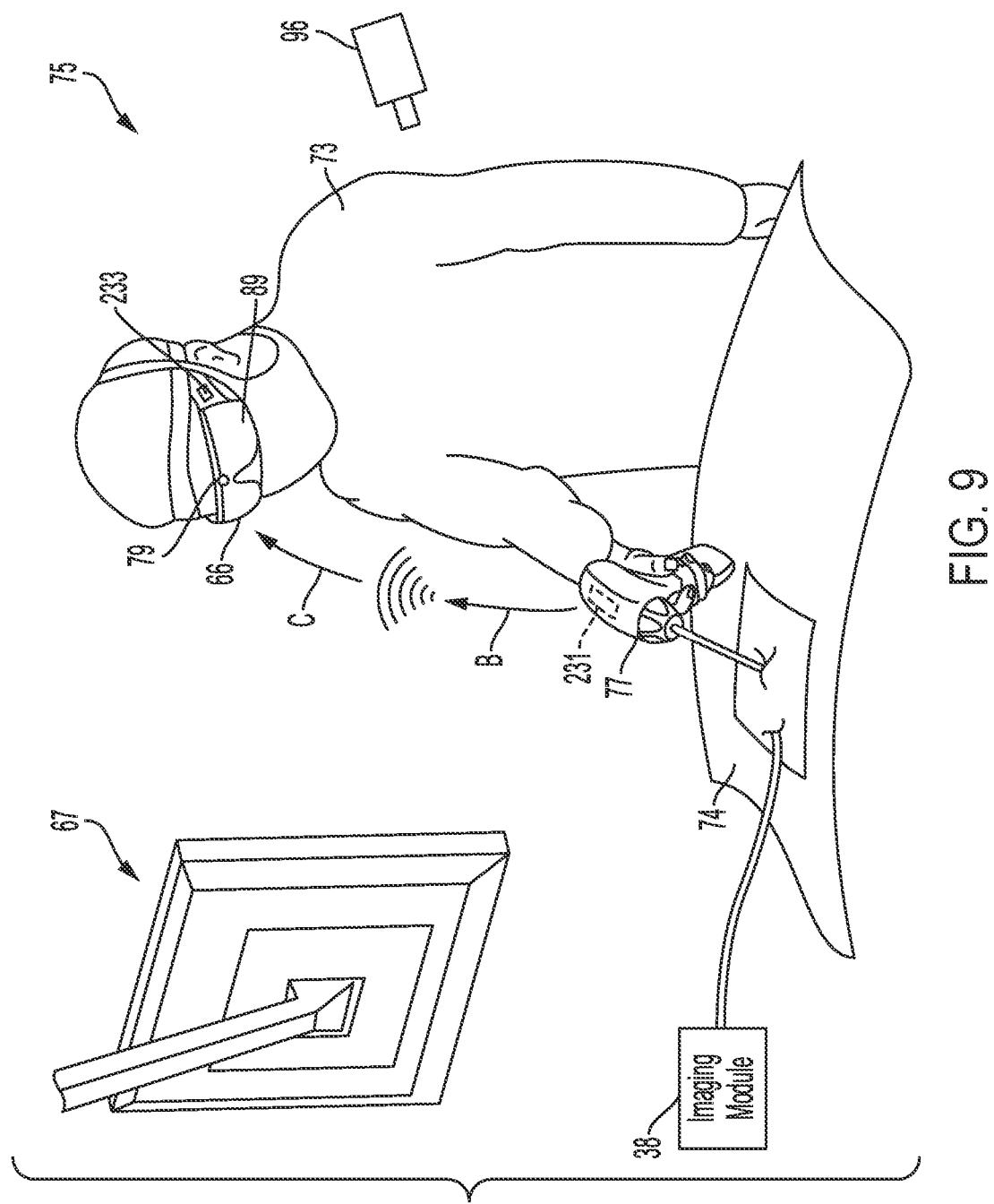
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

Figure 11:
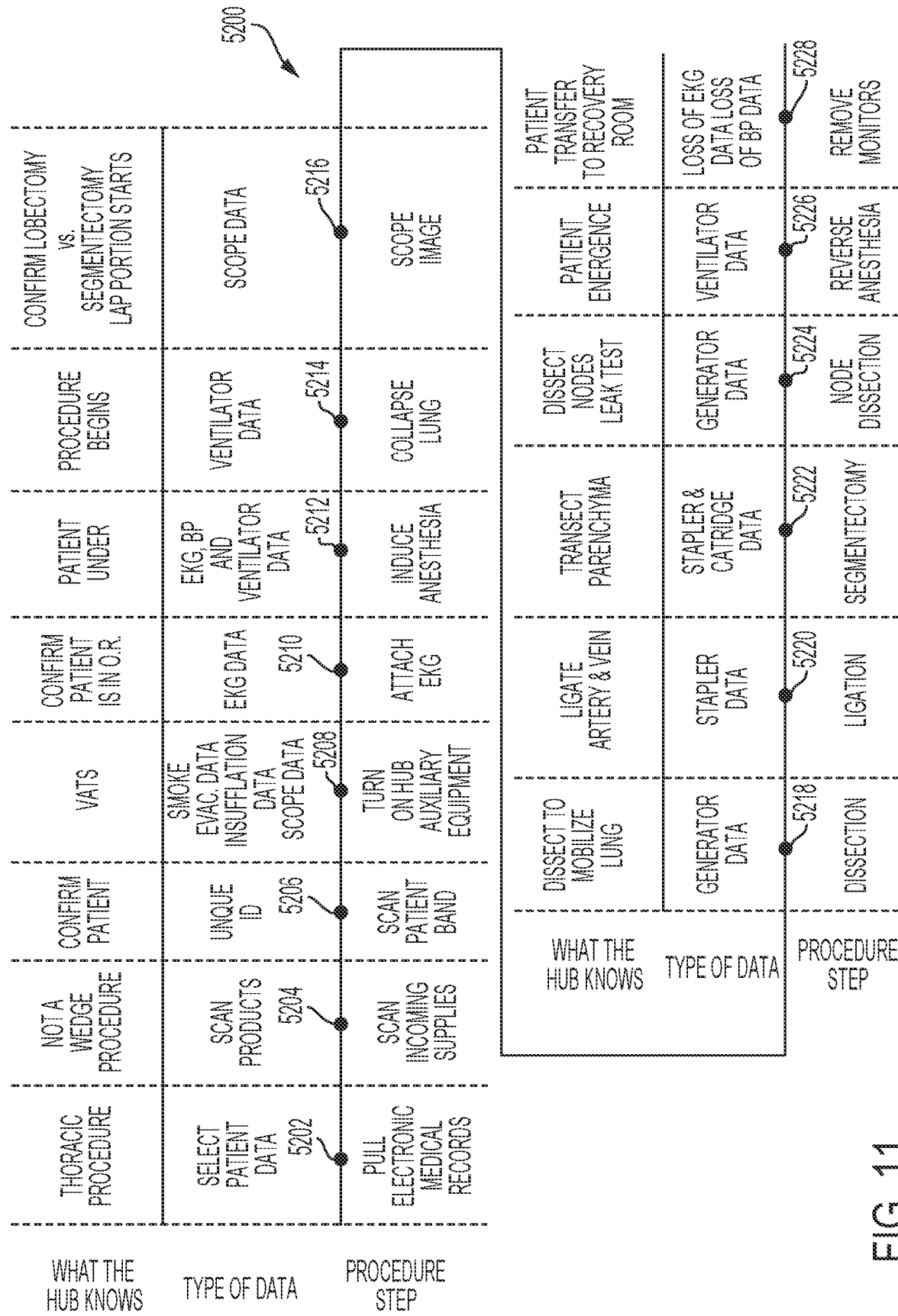
FIG. 11 illustrates a timeline of a situational awareness surgical procedure, according to one aspect of this disclosure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 11, the patient data can also be utilized by a situationally aware surgical hub 5104 to generate control adjustments for the paired modular devices 5102.

Cooperative Overlays of Interacting Instruments

Having described a general implementation of the various surgical systems, surgical hubs, communication systems, augmentation systems, and augmented reality devices disclosed herein, such as surgical systems 1, 2, 50, 52, surgical hubs 6, 56, 5104, communication system 63, augmentation system 83, and AR devices 66, 84, the disclosure now turns to describe various other implantations of the systems, hubs, and devices. For the sake of brevity, various details and implementations of the systems, hubs, and devices being described in the following sections, which are similar to the various systems, hubs, and devices described above, are not repeated herein. Any aspect of the systems, hubs, and devices described below can be brought into and/or be implemented by the above systems, hubs, and devices.

Multiple surgical instruments are often present in the operating room (OR) during a surgical procedure. The surgical instruments present can have different functionalities, different operating parameters, and different intended uses. For example, depending on the surgical procedure or step of the surgical procedure that is being performed, it is often desirable, or even required, to use multiple surgical instruments simultaneously. Thus, some of the surgical instruments in the OR during a surgical procedure may be intended to be use simultaneously and/or in close proximity to one another. For example, a circular stapling instrument may be intended to be used with a specific anvil device. As another example, a buttress device may be intended to be used with a specific type of endo-cutter instrument. As yet another example, a staple cartridge may be intended to be used with a specific type of surgical stapling instrument. Moreover, the simultaneous use of multiple surgical instruments may be associated with various recommended functionalities that are not available when the instruments are not used in combination.

However, in other instances, some surgical instruments present in the OR are not intended to be used simultaneously or in close proximity to one another (e.g., because the use of various combinations of surgical instruments may cause one or more the instruments to malfunction). For example, using a metallic instrument in proximity to an energy device could cause arcing from the energy device to the metallic instrument. As another example, using a metallic instrument in proximity to an energy device could cause a change in the normal thermal spread of the energy device leading to incomplete seals or device failure. As yet another example, a staple cartridge may be counterfeit and therefore should not be used with a specific surgical stapling instruments. Furthermore, whether or not surgical instruments should be used together may depend on the specific type of surgical instrument being used and the specific surgical procedure that is being performed.

Given the wide variety of combinations of different types surgical instruments that may be present in the OR and the wide variety of different surgical procedures that may be performed, it may be difficult for OR staff to keep track of which combinations of surgical instruments are associated with various functionalities, which combinations of surgical instruments should be used simultaneously and/or in close proximity to one another, and which combinations of surgical instruments should not be used simultaneously and/or in close proximity to one another. Accordingly, there is a need for apparatuses, systems, and methods for determining the presence and/or use of various combinations surgical instruments within the OR, for identifying additional functionality that may available based on the determined combination, for determining that surgical instruments are intended to be used proximately to one another, and/or for determining that surgical instruments are not intended to be used proximately to one another.

Moreover, in cases were multiple surgical instruments are used simultaneously during a surgical procedure or a step of a surgical procedure, the surgical instruments are often interacting with each other and/or with a common object within the surgical field. For example, a surgical grasping device may be used to hold or stabilize tissue while an endo-mechanical surgical device is used to cut the same tissue. As explained above, augmented reality (AR) devices may be used to display virtual objects, data, or visual effects overlaid on images of a surgical field. Thus, in the case of the exemplary surgical grasping device and endo-mechanical surgical device, an AR device may be used to display overlays with information related to each surgical devices' individual interactions with the tissue (e.g., force exerted on the tissue). However, when multiple surgical instruments are interacting with each other and/or a common object, the interaction often results in some combined effect that is different than the effect caused by any one of the individual surgical instruments. Knowledge of this combined effect may be useful to aid OR staff during the performance of the surgical procedure. Thus, in addition to the need for apparatuses, systems, and methods for determining the presence and/or use of various combinations surgical instruments within the OR, there is also a need for apparatuses, systems, and methods for displaying cooperative AR overlays based on interactions between multiple surgical instruments.

Apparatuses, systems, and methods for determining the presence and/or use of various combinations surgical instruments within the OR are disclosed herein. Also disclosed herein are apparatuses, systems, and methods for determining the functionality that may available based on a determined combination of surgical instruments that are present and/or in use during a surgical procedure. As described above, various surgical system configurations may be implemented to communicatively couple multiple surgical instruments within an OR (e.g., operating theater) to one or more surgical hubs. For example, referring again to FIGS. 5 and 6, a computer-implemented interactive surgical system 50 can include at least one surgical hub 56 communicatively coupled to multiple operating theater devices (e.g., multiple surgical instruments 21, 98, 99, etc. within the OR). The surgical hub 56 can be configured to determine the combination of specific surgical instruments that are connected thereto (instrument types, instrument models, instrument settings and functionality, etc.) and/or the combination of specific surgical instruments that are present with a specific OR. Further, the surgical hub 56 can be configured to determine the combination of specific surgical instruments that are being used for a given surgical procedure. It should be noted that although surgical system 50 and surgical hub 56 are referenced in this section as an exemplary surgical system and surgical hub, any of the surgical systems and hubs disclosed herein can be configured to determine the presence and use of specific combinations of surgical instruments.

In various aspects, the connection and/or activation of specific surgical instruments and/or specific combinations of surgical instruments can enable functionality related to the hub and/or the surgical instruments. In one aspect, the connection and/or activation of a specific surgical instrument (surgical device) can enable functionality on the hub. In another aspect, the connection and/or activation of a specific combination of surgical instruments can enable functionality on the hub. The hub functionality may be enabled based on information stored within a memory of the surgical instrument or instruments that are connected thereto. Moreover, the hub functionality enabled may involve unlocking additional modes and/or features that can be executed by the hub. These additional modes and/or features may be related to the specific instrument or combination of instruments that, by connection to the surgical hub, enabled the hub functionality. For example, a specific surgical instrument such as a specific model and/or revision of an energy device may contain information mapped within its electrically erasable programmable read-only memory (EEPROM) that is read upon connection to the surgical hub. The EEPROM-stored information may cause additional features and/or modes to be unlocked on the hub. As another example, the connection of the combination of a specific model of an energy device and a specific model of an endoscope may cause additional features and/or modes to be unlocked on the hub.

In another aspect, the connection and/or activation of a specific surgical instrument (surgical device) or a specific combination of surgical instruments can enable functionality on the surgical instrument and/or instruments. The instrument functionality enabled by the surgical hub may include configuring the surgical instrument and/or instruments by the surgical hub. For example, upon connection, the surgical hub may cause a surgical instrument to prompt the user to input a setting selection or a user profile related to the connected instrument or combination of instruments. The instrument functionality enabled by connection of a surgical instrument or combination of instruments to the surgical hub may include automatically updating a configuration of the surgical instrument and/or instruments based on setting of the surgical hub. For example, upon connection, based on the settings of the surgical hub, the surgical hub may cause a surgical instrument to include an additional button (e.g. a touch screen button). The additional button may relate to an additional operation or function of the instrument that is available based on the combination of surgical instruments connected to the surgical hub.

In yet another aspect, the connection and/or activation of a specific surgical instrument (surgical device) or a specific combination of surgical instruments can cause the hub to change a parameter of the surgical instrument and/or instruments. For example, connecting a specific combination of surgical instruments to the surgical hub may cause the hub to adjust a clamping pressure, knife speed, maximum articulation angle, and/or firing stroke setting of an end effector of one of the connected surgical instruments. Any of the surgical instrument parameters that are adjusted by the hub may be adjusted or customized by the user.

In yet another aspect, the connection and/or activation of a specific surgical instrument (surgical device) or a specific combination of surgical instruments can cause parameters of the surgical hub to be adjusted. For example, the surgical hub may include an algorithm for optimizing ideal and/or targeted firings and angles for a specific surgical procedure, such as a sleeve gastrectomy. The hub could be configured to update the algorithm depending on the specific surgical instrument that is activated during the procedure (e.g., the algorithm can be updated depending on whether the active linear endo-cutter is a 45 mm endo-cutter or a 60 mm endo-cutter).

Figure 12:
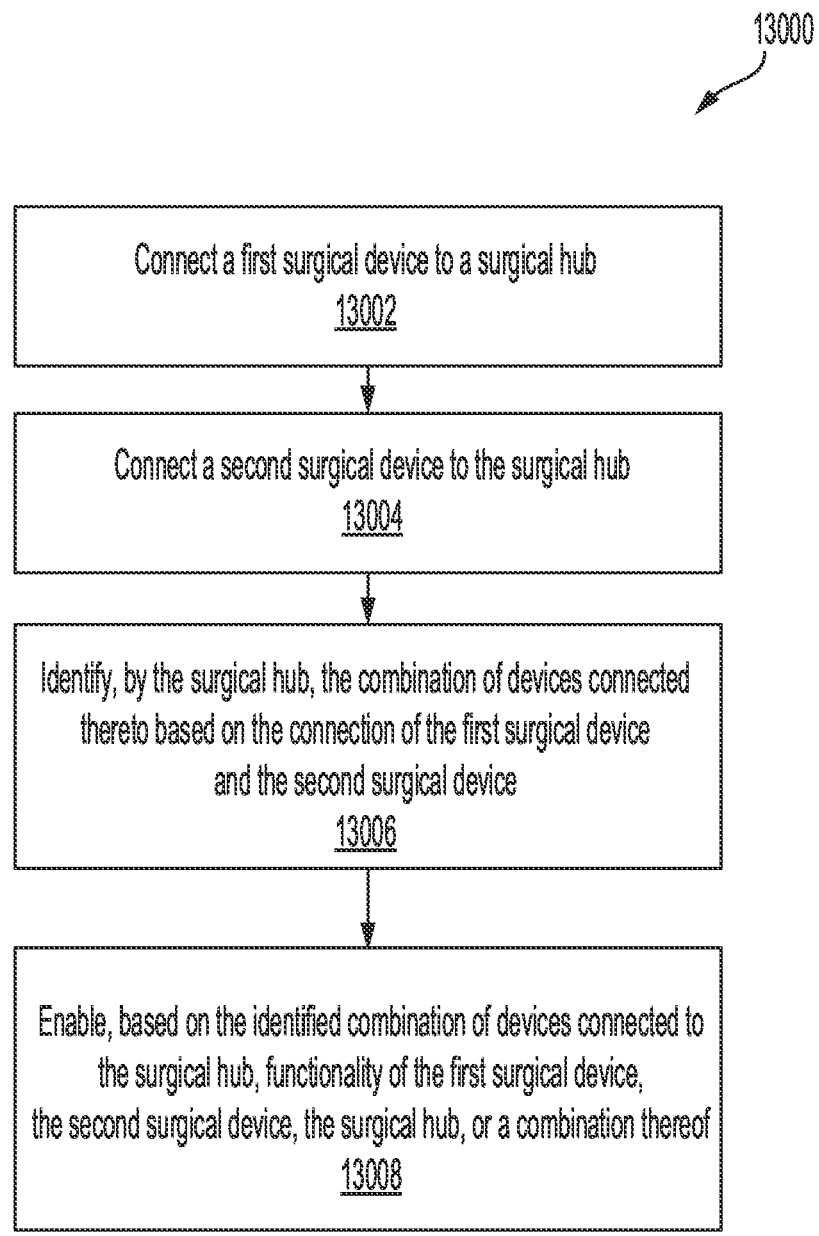
FIG. 12 illustrates a flowchart of a method for enabling functionality based on combinations of connected surgical devices, according to one aspect of this disclosure, according to one aspect of this disclosure.

FIG. 12 illustrates method 13000 for enabling functionality based on combinations of connected surgical devices, according to several non-limiting aspects of this disclosure. The method 13000 can include connecting 13002 a first surgical device to a surgical hub and connecting 13004 a second surgical device to the surgical hub. Further, the method 13000 can include identifying 13006, by the surgical hub, the combination of devices connected thereto based on the connection 13002 of the first surgical device and the connection 13004 of the second surgical device. The method 13000 can further include enabling 13008, based on the identified 13006 combination of devices connected to the surgical hub, functionality of the first surgical device, the second surgical device, the surgical hub, or a combination thereof.

Apparatuses, systems, and methods for determining that surgical instruments are intended to be used together (e.g., in proximity to one another) and for determining that surgical instruments are not intended to be used together are disclosed herein. As explained above, various surgical system configurations may be implemented to communicatively couple multiple surgical instruments within an OR (e.g., operating theater) to one or more surgical hubs. For example, referring again to FIGS. 5 and 6, a computer-implemented interactive surgical system 50 can include at least one surgical hub 56 communicatively coupled to multiple operating theater devices (e.g., multiple surgical instruments 21, 98, 99, etc. within the OR). The surgical hub 56 can be configured to determine the combination of specific surgical instruments that are connected thereto. Further, the surgical hub 56 can be configured to determine the combination of specific surgical instruments that are being used for a given surgical procedure. In one aspect, the surgical hub 56 may store information related to the intended uses of various types of surgical instrument and/or combinations of various types of surgical instruments. In another aspect, the surgical hub 56 may be in communication with a server or other device that stores information related to the intended uses of various types of surgical instrument and/or combinations of various types of surgical instruments. Thus, the surgical hub 56 can be configured to determine, based on the determined combination of surgical instruments connected thereto, that connected surgical instruments are intended to be used together and/or that connected surgical instruments are not intended to be used together. The surgical hub may provide a notification to one or more users (e.g., OR staff) based on the determination of whether or not the connected surgical instruments are intended to be used together. This notification may be in the form of an AR overlay.

However, some surgical instruments may not have the capability to connect to the surgical hub (e.g., surgical instruments may not be smart devices/instruments). Thus, in various aspects, any of the surgical instruments disclosed herein that are capable of connecting to the surgical hub may include sensors configured to detect and/or identify other surgical instruments The hub-connecting surgical instruments including sensors may be referred to hereinafter as "smart sensing instruments". In one aspect, the surgical hub may be configured to cause a smarting sensing instruments to send information related to instruments detected and/or identified by the smart sensing instrument to the surgical hub. The surgical hub may use this information to determine if the detected instruments are intended or are not intended be used with the smart sensing instrument. In another aspect, the surgical hub may use this information to enhance location data used to generate AR overlays related to the detected instruments.

In various aspects, surgical instruments, such as smart sensing instruments and/or instruments that cannot connect to the surgical hub, can include a proximity sensor to detect other instruments. In some aspects, the proximity sensor may be a proximity beacon of a first instrument that sends out a signal including a data set describing the first instrument's functions. A proximity sensor of second surgical instrument may read the incoming signal and determine, based on the data set, whether or not the first instrument and the second surgical instrument are intended to be used in proximity to one another. In one aspect, the second surgical instrument may provide a notification to OR staff based on the determination. In another aspect, the second surgical instrument may send data related to the determination to the surgical hub causing the surgical hub to provide a notification to one or more users (e.g., OR staff) indicating whether or not the first and second surgical instruments are intended to be used together. This notification may be in the form of an AR overlay.

In various aspects, some surgical instruments may include a proximity beacon that can send out a signal but cannot read incoming signals from other instruments. For example, the first surgical instrument described above may be a surgical grasper with a proximity beacon capable of sending out a signal but not capable of reading incoming signals. In this case, the second surgical instrument, for example, an energy device, may include a proximity beacon capable of reading the incoming signal from the first surgical instrument. Thus, the second surgical instrument may be configured to determine if the first and second instruments are intended to be used together.

Figure 13:
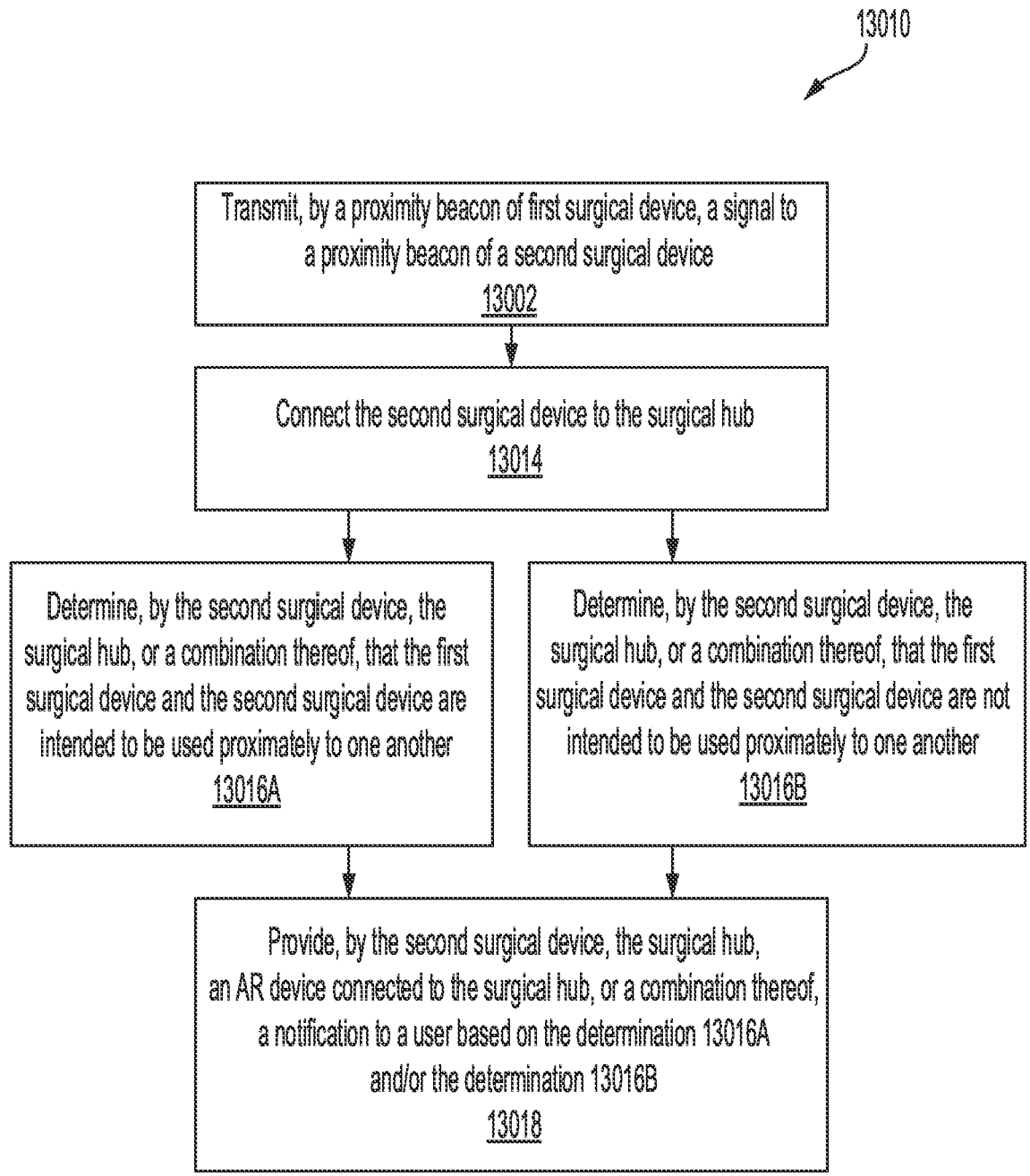
FIG. 13 illustrates a flowchart of a method for determining if multiple surgical instruments are intended to be used in proximity to one another, according to one aspect of this disclosure.

FIG. 13 illustrates a method 13010 for determining whether or not multiple surgical instruments are intended to be used in proximity to one another, according to several non-limiting aspects of this disclosure. The method 13010 can include transmitting 13013, by a proximity beacon of first surgical device, a signal to a proximity beacon of a second surgical device. Further, the method 13010 can include connecting 13014 the second surgical device to a surgical hub. Yet further, in one aspect, the method 13010 can include determining 13016A, by the second surgical device, the surgical hub, or a combination thereof, that the first surgical device and the second surgical device are intended to be used proximately to one another. In another aspect, the method 13010 can include determining 13016B, by the second surgical device, the surgical hub, or a combination thereof, that the first surgical device and the second surgical device are not intended to be used proximately to one another. In some aspects, the method 13010 can also include providing 13018, by the second surgical device, the surgical hub, an AR device connected to the surgical hub, or a combination thereof, a notification to a user (e.g., OR staff) based on the determination 13016A and/or the determination 13016B.

Figure 14:
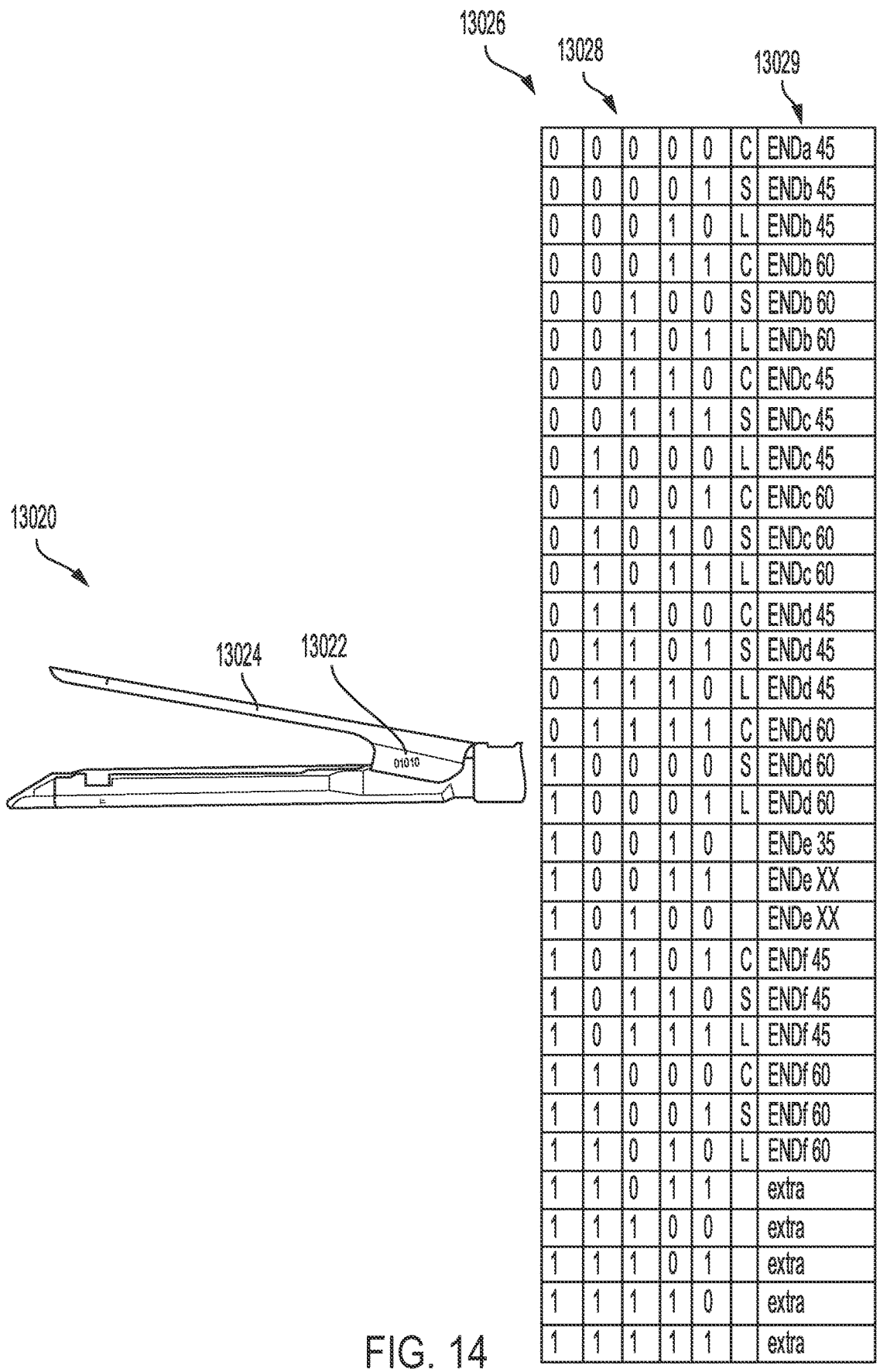
FIG. 14 illustrates a surgical instrument including an identification code as well as a corresponding identification code table, according to one aspect of this disclosure.

In some aspects, the determination of whether or not multiple surgical instruments are intended to be used together may be based on an identification code of at least one of the instruments. For example, FIG. 14 illustrates a surgical instrument 13020 including an identification code 13022 as well as a corresponding identification code table 13026, in accordance with at least one non-limiting aspect of the present disclose. The identification code 13022 can be a set of characters printed or otherwise displayed on a surface 13024 of the instrument 13020. In one aspect, the identification code 13022 may be displayed on multiple surfaces of the instrument 13020 so that the identification code can be viewed from multiple angles (not shown in FIG. 14). The identification code 13022 may include five (5) binary characters 13028, wherein each specific type and/or model 13029 of surgical instrument is associated with a unique combination of the five binary characters. An identification code table 13026 can be used correlate the unique combination of five binary characters 13028 with the type and/or model 13029 of the surgical instrument. In one aspect, the identification code 13022 may be detected by an imaging device associated with an imaging module of the surgical hub (e.g. imaging device 24, 96, AR device 66 referenced with respect to FIG. 2; imaging module 38 referenced with respect to FIG. 3). In another aspect, a user (e.g., OR staff) may manually provide the identification code 13022 to the surgical hub. Thus, the surgical hub may be able to identify the surgical instrument 13020 based on the identification code 130222 and determine if the identified surgical instrument 13020 is intended to be used with other detected instruments.

In various aspects, apparatuses, systems, and methods for displaying cooperative AR overlays based on interactions between multiple surgical instruments are disclosed herein. As explained above, augmented reality (AR) devices (e.g., AR device 66) may be used to generate an image of a surgical field during a surgical procedure, for example, based on images of the surgical field captured by one or more imaging devices of a surgical system (e.g. imaging device 24, 96, AR device 66 referenced with respect to FIG. 2; imaging module 38 referenced with respect to FIG. 3). The image generated by the AR device can be a still image or a live feed of the surgical field. Further, the image of the surgical field generated by the AR device can sometimes be referred to hereinafter as an intraoperative display.

As explained in more detail above, the surgical systems and/or surgical hubs disclosed herein (such as surgical systems 1, 2, 50, 52, surgical hubs 6, 56, 5104) can be configured to cause the AR device to display a virtual objects, data, or visual effects overlaid on the intraoperative display. These virtual objects, data, and visual effects can be based on various attributes of a surgical instrument, for example, as the surgical instrument is performing a surgical procedure in the surgical field. In other words, the intraoperative display can display a virtual data overlay including objects, data, and/or visual effects related to the use of a surgical instrument in the surgical field. For example, the intraoperative display can display data related the effect a surgical instrument has on tissue as the surgical instrument interacts with tissue in the surgical field.

As also explained in more detail above, multiple surgical instruments may be used simultaneously when performing a surgical procedure. Further, the surgical hub and/or the individual instruments can be configured to detect the combination specific combination of surgical instruments are in use. In other aspects, the surgical hub and/or the individual instruments can be configured to detect an interaction between the combination of instruments. In one aspect, the detected interaction can include the surgical instruments interacting with each other. In another aspect, the detected interaction can include the instruments interacting with a common structure within the surgical field, such as, for example tissue. Thus, the intraoperative display can be configured to display a data overlay based on the interaction between the combination of surgical instruments.

In some aspects, the intraoperative display can be configured to display multiple data overlays based on the use of multiple instruments. For example, a first surgical instrument may be simultaneously present in the surgical field with a second surgical instruments. The surgical hub may receive data related to the operation of the first surgical instrument and data related to the operation of the second surgical instrument. The data related to the operation of the first surgical instrument can be used to display generate a first data overlay and data related to the operation of the second surgical instrument can be used to generate a second data overlay. The first data overlay and the second data overlay can be simultaneously displayed by the intraoperative display. Thus, a surgeon using the AR device may be able to simultaneously receive information related to both instruments.

In some aspects, multiple users (e.g., multiple OR staff members) may each be using an AR device. In other aspects, multiple users may each be using a surgical instrument. The surgical systems and/or surgical hubs disclosed herein can be configured to cause any combination of different AR devices to display any number and combination of different data overlays based on the use of multiple surgical instruments. For example, a first user may be using a first AR device generating a first intraoperative display. The surgical hub can be configured to link the first AR device to the first user. A second user may be using a second AR device generating a second intraoperative display. The surgical hub can be configured to link the second AR device to the second user. Further, the first user may be using a first surgical instrument and the second user may be using a second surgical instrument. The first interactive display can be configured to display a first data overlay based on the first instrument and a second data overlay based on the second instrument. Likewise, the second interactive display can be configured to display the first data overlay based on the first instrument and the second data overlay based on the second instrument. In another example, the first intraoperative display may only display the first data overlay based on the first user's use of the first instrument and not the second instrument. Thus, the data overlays displayed by each intraoperative display can be customized based on which user the AR device is linked to, the preferences of the user, the surgical instrument the user is using, or any combination thereof.

Moreover, as surgical instruments are used in combination, data related to various attributes of the combined use of the surgical instruments can be detected, calculated, and/or otherwise determined by the surgical hub, the individual instruments, other components of the surgical system, or a combination thereof. Thus, the intraoperative display can be configured to display a data overlay based on an attributed related to the combined use of the surgical instruments. This type of data overlay can sometimes be referred to herein as a cooperative data overlay. Attributes related to the combined use of surgical instruments can include, for example, a combined force exerted by the instrument, a distance between the instruments, a distance between the instruments and an object, a combined parameter of the instruments, or any other attribute that can be detected, calculated, or otherwise determined based on the interaction of multiple surgical instruments. The cooperative data overlay may be displayed with and combination of other data overlays.

Figure 15A:
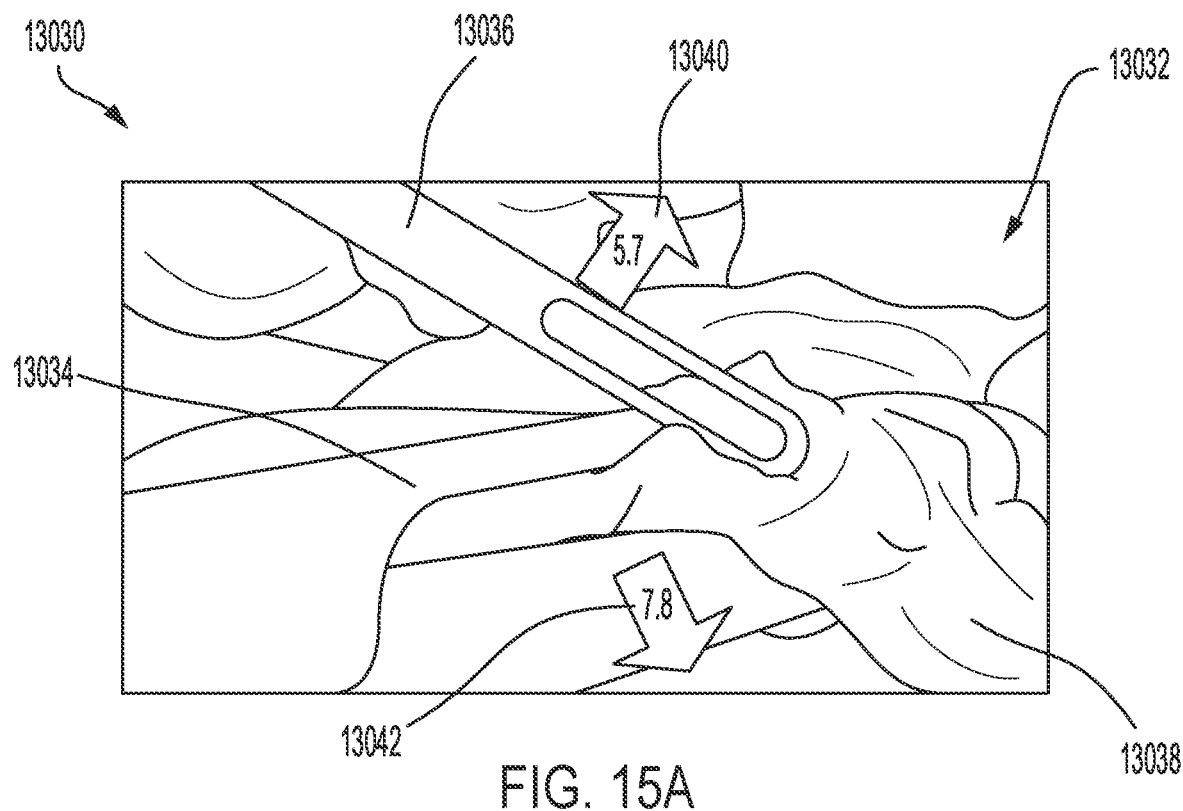
FIGS. 15A and 15B illustrate an exemplary intraoperative display displaying an endo-cutter and a surgical grasper interacting with tissue in a surgical field, according to one aspect of this disclosure.
Figure 15B:
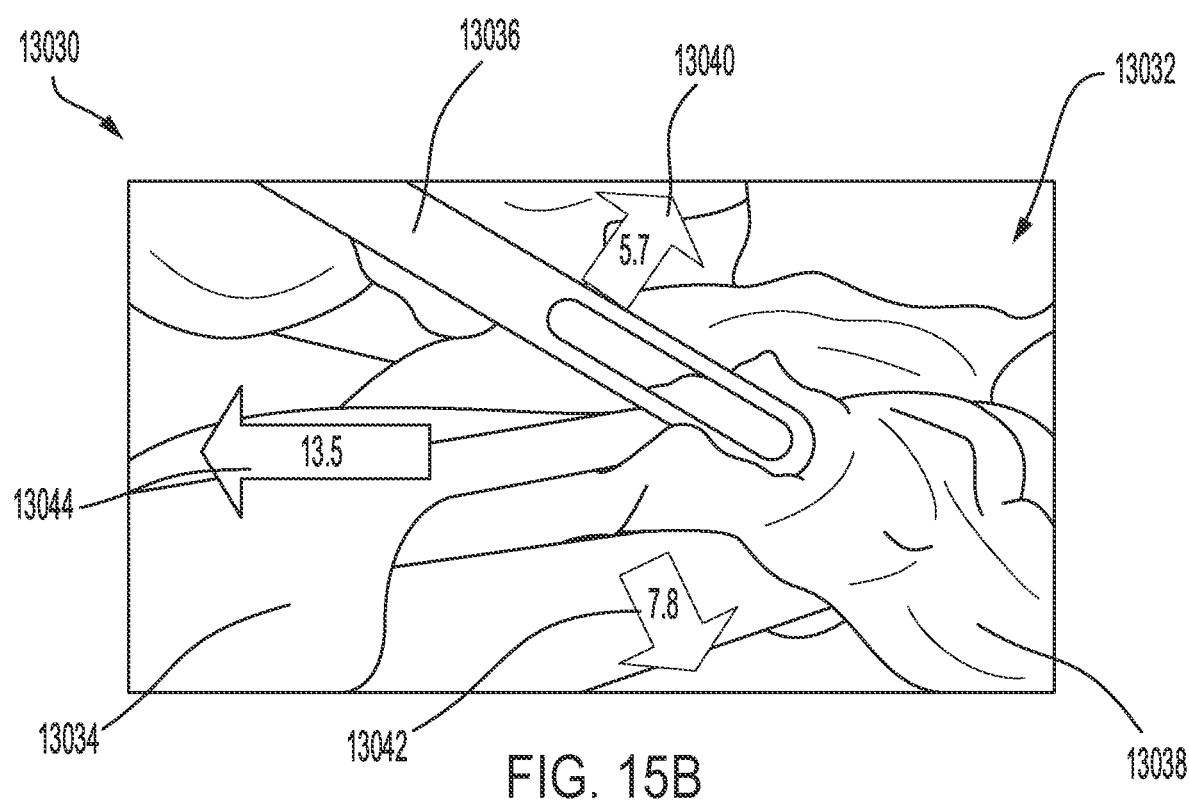

FIGS. 15A and 15B illustrate an exemplary intraoperative display 13030 displaying an endo-cutter 13034 and a surgical grasper 13036 interacting with tissue 13038 in a surgical field 13032, in accordance with several non-limiting aspects of this disclosure. Referring now to FIG. 15A, the endo-cutter 13034 can be seen grasping the tissue 13038. This grasping action causes a tension force on the tissue 13038. In some aspects, the tension force can be determined by a surgical hub. Based on the interaction of the surgical grasper 13036 and the tissue 13038, a first data overlay 13040 is displayed by the intraoperative display 13030. The first data overlay 13040 includes a vector arrow depicting the tension force (5.7) and the direction of the tension applied to the tissue 13038 by the surgical grasper 13036. FIG. 15A also depicts an endo-cutter 13034 grasping the tissue 13038. This grasping action also causes a tension force on the tissue 13038 which, in some aspects, can be determined by a surgical hub. Based on the interaction of the endo-cutter 13034 and the tissue 13038, a second data overlay 13042 is displayed by the intraoperative display 13030. The second data overlay 13042 includes a vector arrow depicting the tension force (7.8) and the direction of the tension applied to the tissue 13038 by the surgical grasper 13036.

Referring now to FIG. 15B, a cooperative data overlay 13044 is displayed by the intraoperative display 13030. The cooperative data overlay 13044 includes a vector arrow depicting a combined tension force (13.5) and direction of the tension applied to the tissue 13038 by the combined interaction of the endo-cutter 13034 and the surgical grasper 13036. The combined tension force and direction of tension shown by the cooperative data overlay 13044 can be calculated or otherwise determined by the surgical hub. Thus, a user viewing the intraoperative display 13030 including the cooperative data overlay 13044, is able to easily visualize the combined effect that the endo-cutter 13034 and the surgical grasper 13036 are causing to the tissue 13038.

Figure 16A:
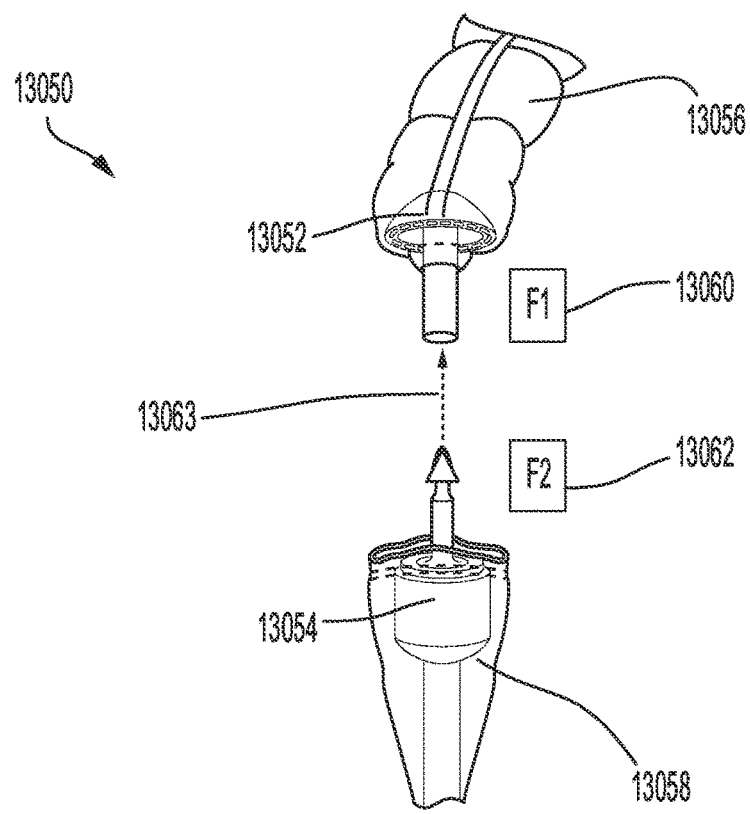

FIGS. 16A, 16B, 16C, and 16D illustrate an exemplary intraoperative display 13050 displaying the performance of an anastomosis procedure using an anvil 13052 and a device deck 13054, in accordance with several non-limiting aspects of this disclosure. Referring now to FIG. 16A, the anvil 13052 can be seen interfacing with a first section of a colon 13056. As the first section of the colon 13056 is advanced 13063 towards the device deck 13054, the anvil 13056 exerts a pulling force F1 on the surrounding tissue of the first section of the colon 13056. This force can be determined by the surgical hub. Based on the interaction of anvil 13056 and the first section of the colon 13056, a first data overlay 13060 is displayed by the intraoperative display 13050. The first data overlay 13060 can include graphic indicating the pulling force of the anvil 1352 on the first section of the colon 13056 as well as the directionality of the force. FIG. 16A also depicts device deck 13054 interfacing with a second section of a colon 13058. As the second section of the colon 13058 is advanced 13063 towards the anvil 13052, the device deck 13054 exerts a pulling force F2 on the surrounding tissue of the second section of the colon 13058. This force can be determined by the surgical hub. Based on the interaction of device deck 13054 and the second section of the colon 13058, a second data overlay 13062 is displayed by the intraoperative display 13050. The second data overlay 13062 can include graphic indicating the pulling force of the device 13060 on the second section of the colon 13058 as well as the directionality of the force.

Figure 16B:
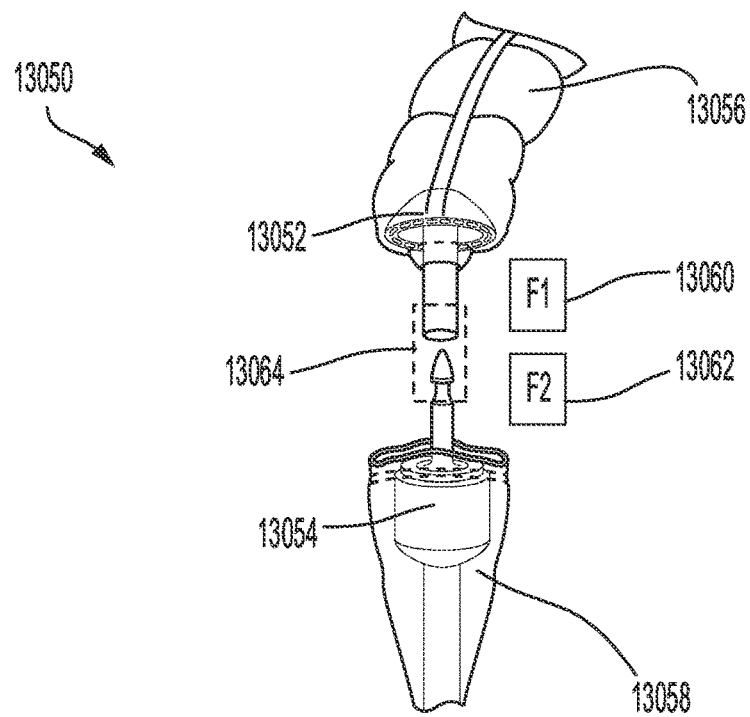

Referring now to FIG. 16B, the intraoperative display 13050 now depicts the anvil 13052 and the device deck 13054 as they are nearing attachment. The surgical hub can be configured to sense the proximity of the anvil 13052 and the device deck 13054. Further, the surgical hub can be configured to display a first cooperative overlay 13064 based on the sensed proximity. The first cooperative overlay 13064 can graphically indicate whether or not attachment between the anvil 13052 and the device deck 13054 has been achieved. For example, the first cooperative overlay 13054 as shown in FIG. 16B can indicate that attachment between the anvil 13052 and the device deck 13054 has not yet been achieved. The first data overlay 13060, the second data overlay 13062, and the first cooperative overlay 13064 can assist a user viewing the intraoperative display 13050. In some aspects, the intraoperative display 13050 can also include additional data overlays to indicate a predicted change in the forces applied to the colon tissue. In other aspects, the intraoperative display 13050 can include additional data overlays to indicate an optimal angle of approach. These data overlays may assist the user in achieving an optimal outcome of the anastomosis procedure.

Figure 16C:
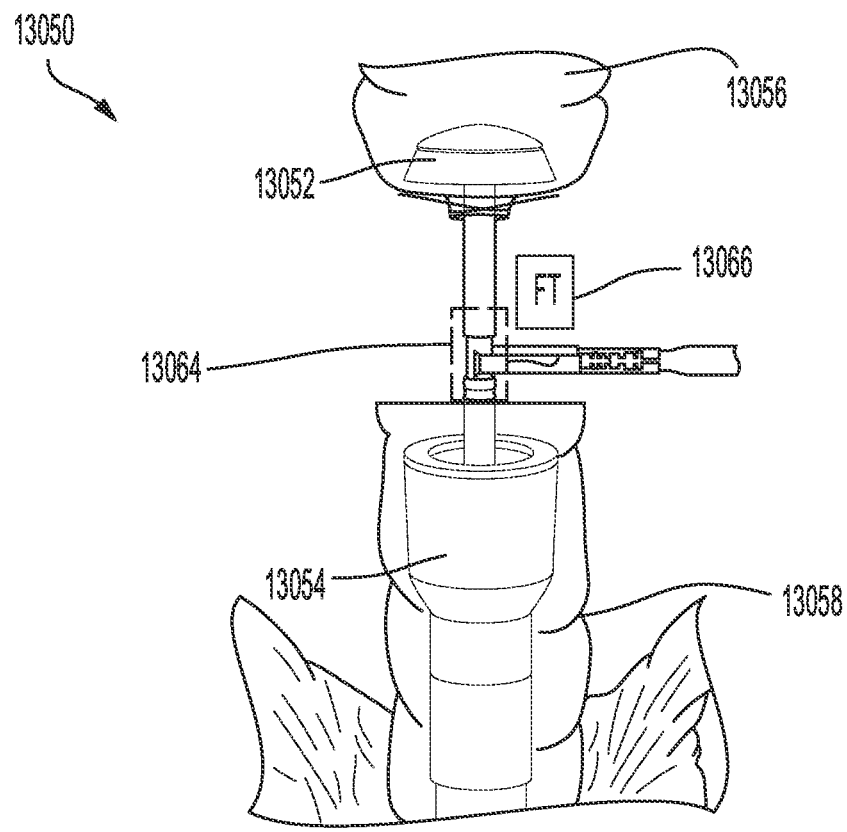

Referring now to FIG. 16C, the intraoperative display 13050 now depicts attachment of the anvil 13052 and the device deck 13054 by a device 13068. The surgical hub can be configured to determine this attachment. Based on the attachment, the first cooperative overlay 13064 now graphically indicates the attachment. As a result of the attachment, the intraoperative display 13050 now depicts a second cooperative overlay 13066. The second cooperative overlay 13066 can include a graphic indicating the combined pulling force FT of the anvil 13052 and the device deck 13054. In the non-limiting aspect of FIG. 16C, the attachment of the anvil 13052 and the device deck 13054 causes the first data overlay 13060 and the second data overlay 13062 to no longer be displayed by the intraoperative display. In other aspects, the first data overlay 13060 and the second data overlay 13062 may remain displayed upon attachment of the anvil 13052 to the device deck 13054.

Figure 16D:
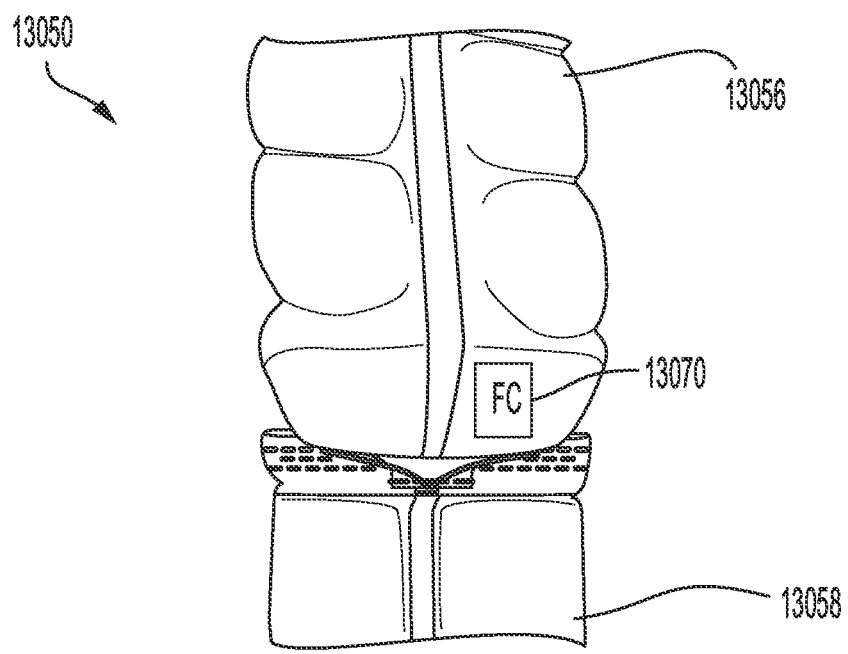

Referring now to FIG. 16D, the intraoperative display 13050 now depicts the compression of the first section of the colon 13056 and the second section of the colon 13058 during anastomosis. The surgical hub can be configured to determine the compression force FC on the first section of the colon 13056 and the second section of the colon 13058 during this portion of the procedure. The compression force can be a force caused by compression of the tissue between the anvil 13052 and the device deck 13054. Accordingly, the intraoperative display 13050 can display a third cooperative overlay 13070 that graphically depicts the compression force FC. The third cooperative overlay 13070 can be used by the user to ensure that there is a good seal and acceptable staple formation across the first section of the colon 13056 and the second section of the colon 13058.

FIG. 17 illustrates a method 13200 for displaying a cooperative overlay of interacting instruments, according to several non-limiting aspects of this disclosure. The method 13200 may be practiced by any combination of the surgical systems, surgical hubs, communication systems, augmentation systems, AR devices, any of the components thereof, and any other devices and systems disclosed herein, such as surgical systems 1, 2, 50, 52, surgical hubs 6, 56, 5104, communication system 63, augmentation system 83, and AR devices 66, 84.

In accordance with the method 13200, a first augmented reality display device may be communicatively coupled 13202 to a surgical hub. The first augmented reality device can generate 13204 a first intraoperative display of a surgical field. The first intraoperative display can display 13206 a first data overlay based on operation of a first surgical instrument. The first surgical instrument can interact 13208 with a second surgical instrument and, based on the interaction 13208 of the first and second surgical instrument, the first intraoperative display can display 13210 an indicator of the interaction.

In accordance with one aspect of the method 13200, the interaction 13208 of the first surgical instrument with a second surgical instrument can include the first surgical instrument and the second surgical instrument interacting with a common structure in the surgical field. In another aspect, the first intraoperative display can simultaneously display the first data overlay based on operation of the first surgical instrument and a second data overlay based on operation of the second surgical instrument. In yet another aspect, the first intraoperative display can display a cooperative data overlay based on the interaction of the first surgical instrument and the second surgical instrument. In yet another aspect, the interaction of the first surgical instrument and the second surgical with the common structure in the surgical field can include interacting the first surgical instrument and the second surgical instrument with tissue. Further, the first intraoperative display can display a combined force applied to the tissue by the first surgical instrument and the second surgical instrument.

In accordance with one aspect of the method 13200, a second augmented reality display device can be communicatively coupled to the surgical hub. The second augmented reality display device can generate a second intraoperative display of the surgical field. The second intraoperative display can display a second data overlay based on operation of the second surgical instrument. Further, the second intraoperative display can display an indicator based on the interaction between the first and second surgical instruments. In another aspect of the method 13200, the surgical hub can link the first surgical instrument and the first display device to a first user and link the second the surgical instrument and the second display device to a second user.

In accordance with one aspect of the method 13200, the surgical hub can identify that the first surgical instrument and the second surgical instrument are intended to be operated proximately to one another. In another aspect, the surgical hub can identify that the first surgical instrument and the second surgical instrument are not intended to be operated proximately to one another. In yet another aspect, a proximity sensor of the first surgical instrument can detect the second surgical instrument.

Various additional aspects of the subject matter described herein are set out in the following numbered examples:

Example 1: A method for displaying a cooperative overlay of interacting instruments, the method comprising: communicatively coupling a first augmented reality display device to a surgical hub; generating, by the first augmented reality display device, a first intraoperative display of a surgical field; displaying, by the first intraoperative display, a first data overlay based on operation of a first surgical instrument; interacting the first surgical instrument with a second surgical instrument; and displaying, by the first intraoperative display, an indicator of the interaction based on the interaction between the first and second surgical instruments.

Example 2: The method of example 1, wherein interacting the first surgical instrument with a second surgical instrument comprises: interacting the first surgical instrument and the second surgical instrument with a common structure in the surgical field.

Example 3: The method of any of examples 1-2, further comprising simultaneously displaying, by the first intraoperative display, the first data overlay based on operation of the first surgical instrument and a second data overlay based on operation of the second surgical instrument.

Example 4: The method of any of examples 1-3, further comprising displaying, by the first intraoperative display, a cooperative data overlay based on the interaction between the first surgical instrument and the second surgical instrument.

Example 5: The method of any of examples 1-4, wherein interacting the first surgical instrument and the second surgical instrument with the common structure in the surgical field comprises interacting the first surgical instrument and the second surgical instrument with tissue, and wherein displaying the cooperative data overlay comprises displaying a combined force applied to the tissue by the first surgical instrument and the second surgical instrument.

Example 6: The method of any of examples 1-5, further comprising: communicatively coupling a second augmented reality display device to a surgical hub; generating, by the second augmented reality display device, a second intraoperative display of the surgical field; displaying, by the second intraoperative display, a second data overlay based on operation of the second surgical instrument; displaying, by the second intraoperative display, an indicator of the interaction based on the interaction between the first and second surgical instruments.

Example 7: The method of any of examples 1-6, further comprising: linking, by the surgical hub, the first surgical instrument and the first display device to a first user; and linking, by the surgical hub, the second the surgical instrument and the second display device to a second user.

Example 8: The method of any of examples 1-7, further comprising determining, by the surgical hub, that the first surgical instrument and the second surgical instrument are intended to be operated proximately to one another.

Example 9: The method of any of examples 1-8, further comprising determining, by the surgical hub, that the first surgical instrument and the second surgical instrument are not intended to be operated proximately to one another.

Example 10: The method of any of examples 1-9, further comprising detecting, by a proximity sensor of the first surgical instrument, the second surgical instrument.

Example 11: A system for displaying a cooperative overlay of interacting instruments comprising: a first augmented reality display device configured to generate a first intraoperative display of a surgical field; a first surgical instrument; a second surgical instrument; and a surgical hub communicatively coupled to the first display device; wherein the first intraoperative display displays a first data overlay based on operation of the first surgical instrument; and wherein an interaction of the first surgical instrument and the second surgical instrument causes the first intraoperative display to display an indicator of the interaction.

Example 12: The system of example 11, wherein the interaction of the first surgical instrument and the second surgical instrument comprises an interaction of the first surgical instrument and the second surgical instrument with a common structure in the surgical field.

Example 13: The system of any of examples 11-12, wherein the first intraoperative display simultaneously displays the first data overlay based on operation of the first surgical instrument and a second data overlay based on operation of the second surgical instrument.

Example 14: The system of any of examples 11-13, wherein the interaction of the first surgical instrument and the second surgical instrument causes the first intraoperative display to display a cooperative data overlay based on the interaction.

Example 15: The system of any of examples 11-14, wherein the common structure is tissue; and wherein the cooperative data overlay comprises a combined force applied to the tissue by the first surgical instrument and the second surgical instrument.

Example 16: The system of any of examples 11-15, further comprising: a second augmented reality display device configured to generate a second intraoperative display of a surgical field, the second display device communicatively coupled to the surgical hub; wherein the second intraoperative display displays a second data overlay based on operation of the second surgical instrument; and wherein the interaction of the first surgical instrument and the second surgical instrument causes the second intraoperative display to display an indicator for the interaction.

Example 17: The system of any of examples 11-16, wherein the first surgical instrument and the first display device are linked to a first user; and wherein the second the surgical instrument and the second display device are linked to a second user.

Example 18: The system of any of examples 11-17, wherein the surgical hub is configured to identify that the first surgical instrument and the second surgical instrument are intended to be operated proximately to one another.

Example 19: The system of any of examples 11-18, wherein the surgical hub is configured to identify that the first surgical instrument and the second surgical instrument are not intended to be operated proximately to one another.

Example 20: The system of any of examples 11-19, wherein the first surgical instrument comprises a proximity sensor to detect the second surgical instrument.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method for displaying a cooperative overlay of interacting instruments, the method comprising:
   determining an operation of a first surgical instrument;
   generating, for displaying via a first intraoperative display of a surgical field, a first data overlay based on the operation of the first surgical instrument;
   detecting an interaction between the first surgical instrument and a second surgical instrument;
   generating, for displaying via the first intraoperative display, an indicator of the interaction based on the interaction between the first surgical instrument and second surgical instrument;
   determining a combined force applied to a tissue by the first surgical instrument and the second surgical instrument; and
   generating, for displaying via the first intraoperative display, an indication of the combined force applied to the tissue by the first surgical instrument and the second surgical instrument.

2. The method of claim 1, wherein the indicator of the interaction between the first surgical instrument and the second surgical instrument is configured to indicate the first surgical instrument and the second surgical instrument interacting with a common structure in the surgical field.

3. The method of claim 1, further comprising:
   causing simultaneously displaying, via the first intraoperative display, the first data overlay based on the operation of the first surgical instrument and a second data overlay based on an operation of the second surgical instrument.

4. The method of claim 1, further comprising:
   generating, for displaying via the first intraoperative display, a cooperative data overlay based on the interaction between the first surgical instrument and the second surgical instrument.

5. The method of claim 1, further comprising:
   generating a second intraoperative display of the surgical field;
   generating, for displaying via the second intraoperative display, a second data overlay based on an operation of the second surgical instrument;
   generating, for displaying via the second intraoperative display, an indicator of the interaction based on the interaction between the first and second surgical instruments.

6. The method of claim 5, wherein the first intraoperative display is associated with a first augmented reality display device, the second intraoperative display is associated with a second augmented reality display device, and the method further comprises:
   linking, by a surgical hub, the first surgical instrument and the first augmented reality display device to a first user; and
   linking, by the surgical hub, the second surgical instrument and the second augmented reality display device to a second user.

7. The method of claim 1, further comprising determining, by a surgical hub, that the first surgical instrument and the second surgical instrument are intended to be operated proximately to one another.

8. The method of claim 1, further comprising determining, by a surgical hub, that the first surgical instrument and the second surgical instrument are not intended to be operated proximately to one another.

9. The method of claim 1, further comprising detecting, by a proximity sensor of the first surgical instrument, the second surgical instrument.

10. A system for displaying a cooperative overlay of interacting instruments comprising:
    a first augmented reality display device configured to generate a first intraoperative display of a surgical field;
    a surgical hub communicatively coupled to the first augmented reality display device;

wherein the first intraoperative display is configured to display a first data overlay based on an operation of a first surgical instrument,
wherein an interaction of the first surgical instrument and a second surgical instrument causes the first intraoperative display to display an indicator of the interaction, and the surgical hub is configured to:
determine a combined force applied to a tissue by the first surgical instrument and the second surgical instrument; and
cause the first intraoperative display to display an indication of the combined force applied to the tissue by the first surgical instrument and the second surgical instrument.

11. The system of claim 10, wherein the interaction of the first surgical instrument and the second surgical instrument comprises an interaction of the first surgical instrument and the second surgical instrument with a common structure in the surgical field.

12. The system of claim 10, wherein the first intraoperative display simultaneously displays the first data overlay based on the operation of the first surgical instrument and a second data overlay based on an operation of the second surgical instrument.

13. The system of claim 10, wherein the interaction of the first surgical instrument and the second surgical instrument causes the first intraoperative display to display a cooperative data overlay based on the interaction.

14. The system of claim 10, further comprising:
a second augmented reality display device configured to generate a second intraoperative display of the surgical field, the second display device communicatively coupled to the surgical hub,
wherein the second intraoperative display is configured to display a second data overlay based on an operation of the second surgical instrument, and
wherein the interaction of the first surgical instrument and the second surgical instrument causes the second intraoperative display to display an indicator for the interaction.

15. The system of claim 14, wherein the first surgical instrument and the first augmented reality display device are linked to a first user; and wherein the second surgical instrument and the second augmented reality display device are linked to a second user.

16. The system of claim 10, wherein the surgical hub is configured to identify that the first surgical instrument and the second surgical instrument are intended to be operated proximately to one another.

17. The system of claim 10, wherein the surgical hub is configured to identify that the first surgical instrument and the second surgical instrument are not intended to be operated proximately to one another.

18. The system of claim 10, wherein the first surgical instrument comprises a proximity sensor to detect the second surgical instrument.

* * * * *